US012648736B2

(12) United States Patent
　　　 Mäkinen

(10) Patent No.: US 12,648,736 B2
(45) Date of Patent: Jun. 9, 2026

(54) WEARING DETECTION TECHNIQUES FOR WEARABLE DEVICES

(71) Applicant: Oura Health Oy, Oulu (FI)

(72) Inventor: Jukka-Tapani Mäkinen, Oulu (FI)

(73) Assignee: Oura Health Oy, Oulu (FI)

( * ) Notice: Subject to any disclaimer, the term of this patent is extended or adjusted under 35 U.S.C. 154(b) by 561 days.

(21) Appl. No.: 17/903,627

(22) Filed: Sep. 6, 2022

(65) Prior Publication Data

US 2023/0079736 A1　　　Mar. 16, 2023

Related U.S. Application Data

(60) Provisional application No. 63/244,233, filed on Sep. 14, 2021.

(51) Int. Cl.
　　*A61B 5/00*　　　　(2006.01)
　　*G01B 11/14*　　　(2006.01)
(52) U.S. Cl.
　　CPC ............ *A61B 5/6844* (2013.01); *A61B 5/681* (2013.01); *A61B 5/6843* (2013.01); *G01B 11/14* (2013.01)
(58) Field of Classification Search
　　CPC ..... A61B 5/6844; A61B 5/681; A61B 5/6843; A61B 5/02438; A61B 5/14551; A61B 5/7475; G01B 11/14; G06F 3/0425; H03K 2217/94108; H03K 17/941
　　See application file for complete search history.

(56) References Cited

U.S. PATENT DOCUMENTS

| | | | |
|---|---|---|---|
| 5,088,817 | A | 2/1992 | Igaki et al. |
| 5,781,511 | A | 7/1998 | Yasukawa et al. |
| 8,280,469 | B2 | 10/2012 | Baker, Jr. |
| 9,517,019 | B2 | 12/2016 | Wang et al. |
| 9,681,840 | B2 | 6/2017 | Choi et al. |
| 9,983,625 | B2 | 5/2018 | Shim et al. |
| 10,172,557 | B2 | 1/2019 | Altebaeumer et al. |
| 10,335,087 | B2 * | 7/2019 | Lee ...................... A61B 5/6843 |
| 10,568,525 | B1 * | 2/2020 | Wu ....................... A61B 5/6824 |
| 10,575,780 | B2 | 3/2020 | Van et al. |
| 10,874,312 | B2 | 12/2020 | Rouvinen et al. |

(Continued)

FOREIGN PATENT DOCUMENTS

| | | | |
|---|---|---|---|
| CN | 105960197 A | 9/2016 | |
| JP | 4476664 B2 * | 6/2010 | ......... A61B 5/02427 |

(Continued)

*Primary Examiner* — Thanh Luu
*Assistant Examiner* — Mai Thi Ngoc Tran
(74) *Attorney, Agent, or Firm* — ArentFox Schiff LLP

(57) ABSTRACT

Methods, systems, and devices for wearing detection are described. A method may include directing light from a light source to a detector using an optical light guide of the wearable device, where the optical light guide includes an optical interface configured to allow at least a portion of the directed light to escape the optical light guide based on a refractive property of a material contacting the optical interface. The method may include measuring, via the detector, an amount of escaped light which escaped the optical light guide, where the amount of escaped light is indicative of a level of surface contact at the optical interface of the optical light guide. The method may further include controlling an activation of one or more sensors of the wearable device based on the amount of escaped light.

14 Claims, 12 Drawing Sheets

(56)     References Cited

U.S. PATENT DOCUMENTS

| | | | |
|---|---|---|---|
| 10,918,289 B1 * | 2/2021 | Wasson ................ | A61B 5/0022 |
| 11,058,311 B2 | 7/2021 | Nakata et al. | |
| 11,172,884 B2 | 11/2021 | Duan et al. | |
| 11,559,216 B1 * | 1/2023 | Mehta ................ | A61B 5/02427 |
| 11,771,350 B1 | 10/2023 | Mannheimer et al. | |
| 11,998,326 B2 | 6/2024 | Ni et al. | |
| 12,066,702 B1 | 8/2024 | Allec et al. | |
| 2010/0149222 A1 * | 6/2010 | Welford ............... | H04N 9/3164 |
| | | | 313/498 |
| 2016/0270677 A1 | 9/2016 | Lin | |
| 2016/0278645 A1 | 9/2016 | Yoon | |
| 2017/0209095 A1 * | 7/2017 | Wagner ............. | A61B 5/02427 |
| 2017/0347957 A1 | 12/2017 | Van et al. | |
| 2020/0037956 A1 | 2/2020 | Kang et al. | |
| 2020/0092634 A1 * | 3/2020 | Wagner ................ | A61B 5/721 |
| 2020/0146630 A1 | 5/2020 | Joe et al. | |
| 2020/0163616 A1 | 5/2020 | Sakaya | |
| 2020/0367827 A1 | 11/2020 | Min et al. | |
| 2023/0081794 A1 | 3/2023 | Mäkinen et al. | |
| 2024/0090784 A1 | 3/2024 | Liu | |

FOREIGN PATENT DOCUMENTS

| | | | |
|---|---|---|---|
| KR | 10-0817272 B1 | 3/2008 | |
| WO | 2005/092179 A1 | 10/2005 | |
| WO | 2015/113054 A1 | 7/2015 | |

* cited by examiner 410-a　410-b 420-a 415-b 420-b 415-a 400-a

405

425-a　　425-b 410-b 420-a 410-a 415-a 420-b 415-b 400-b

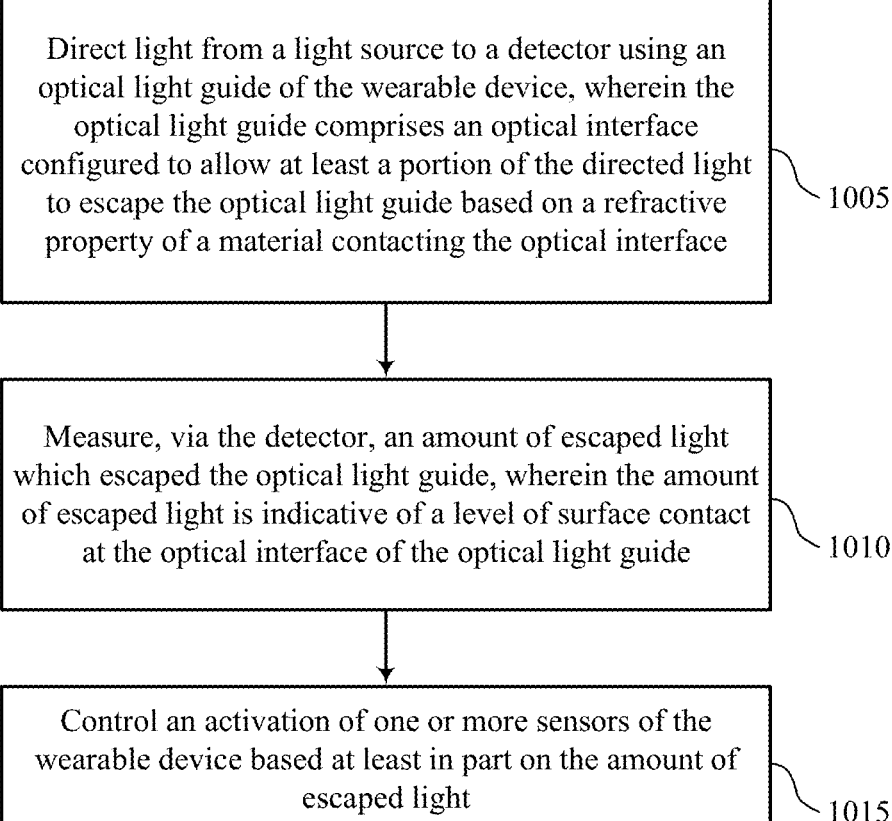

Direct light from a light source to a detector using an optical light guide of the wearable device, wherein the optical light guide comprises an optical interface configured to allow at least a portion of the directed light to escape the optical light guide based on a refractive property of a material contacting the optical interface

1005

Measure, via the detector, an amount of escaped light which escaped the optical light guide, wherein the amount of escaped light is indicative of a level of surface contact at the optical interface of the optical light guide

1010

Control an activation of one or more sensors of the wearable device based at least in part on the amount of escaped light

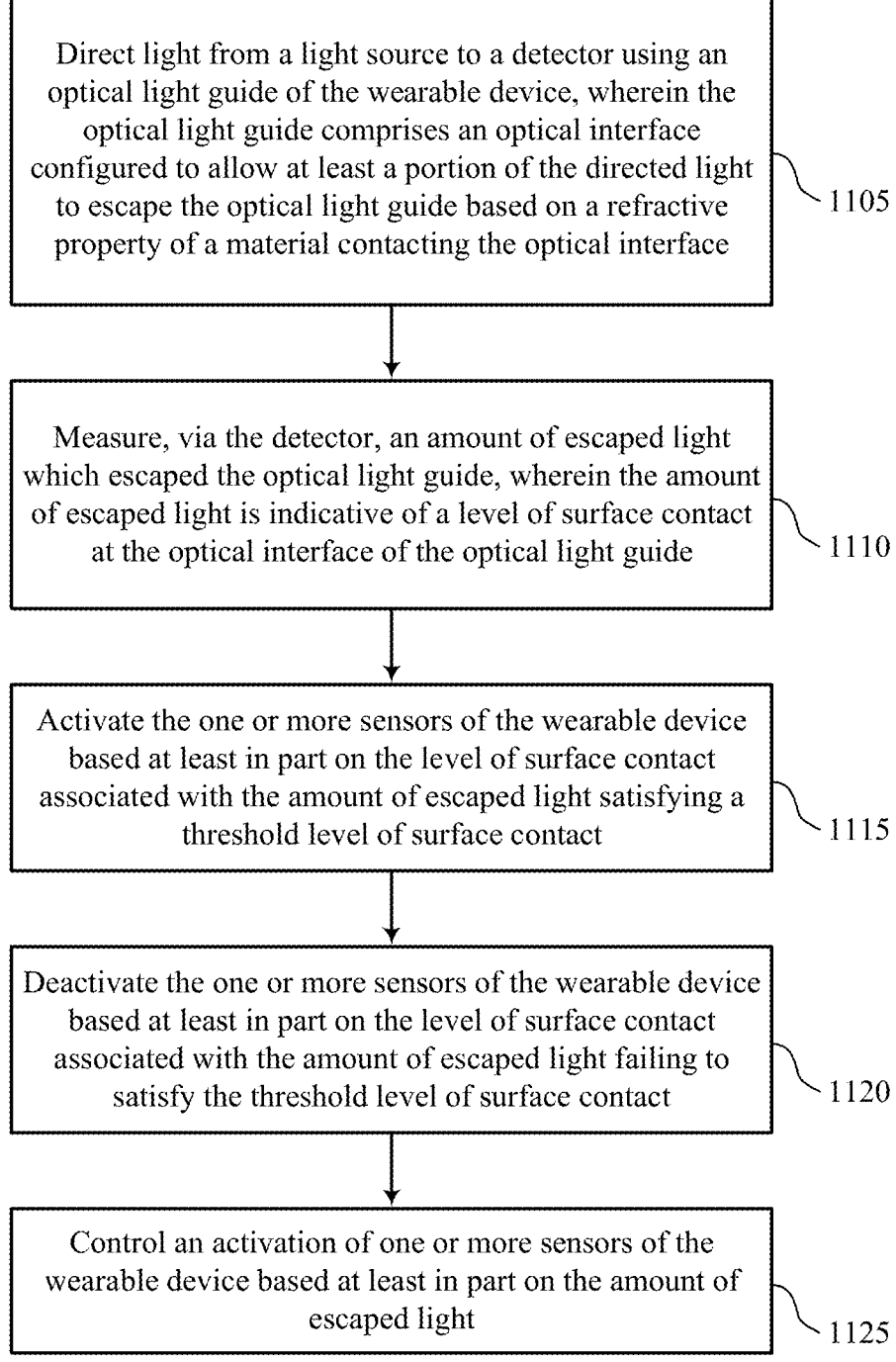

Direct light from a light source to a detector using an optical light guide of the wearable device, wherein the optical light guide comprises an optical interface configured to allow at least a portion of the directed light to escape the optical light guide based on a refractive property of a material contacting the optical interface

1105

Measure, via the detector, an amount of escaped light which escaped the optical light guide, wherein the amount of escaped light is indicative of a level of surface contact at the optical interface of the optical light guide

1110

Activate the one or more sensors of the wearable device based at least in part on the level of surface contact associated with the amount of escaped light satisfying a threshold level of surface contact

1115

Deactivate the one or more sensors of the wearable device based at least in part on the level of surface contact associated with the amount of escaped light failing to satisfy the threshold level of surface contact

1120

Control an activation of one or more sensors of the wearable device based at least in part on the amount of escaped light

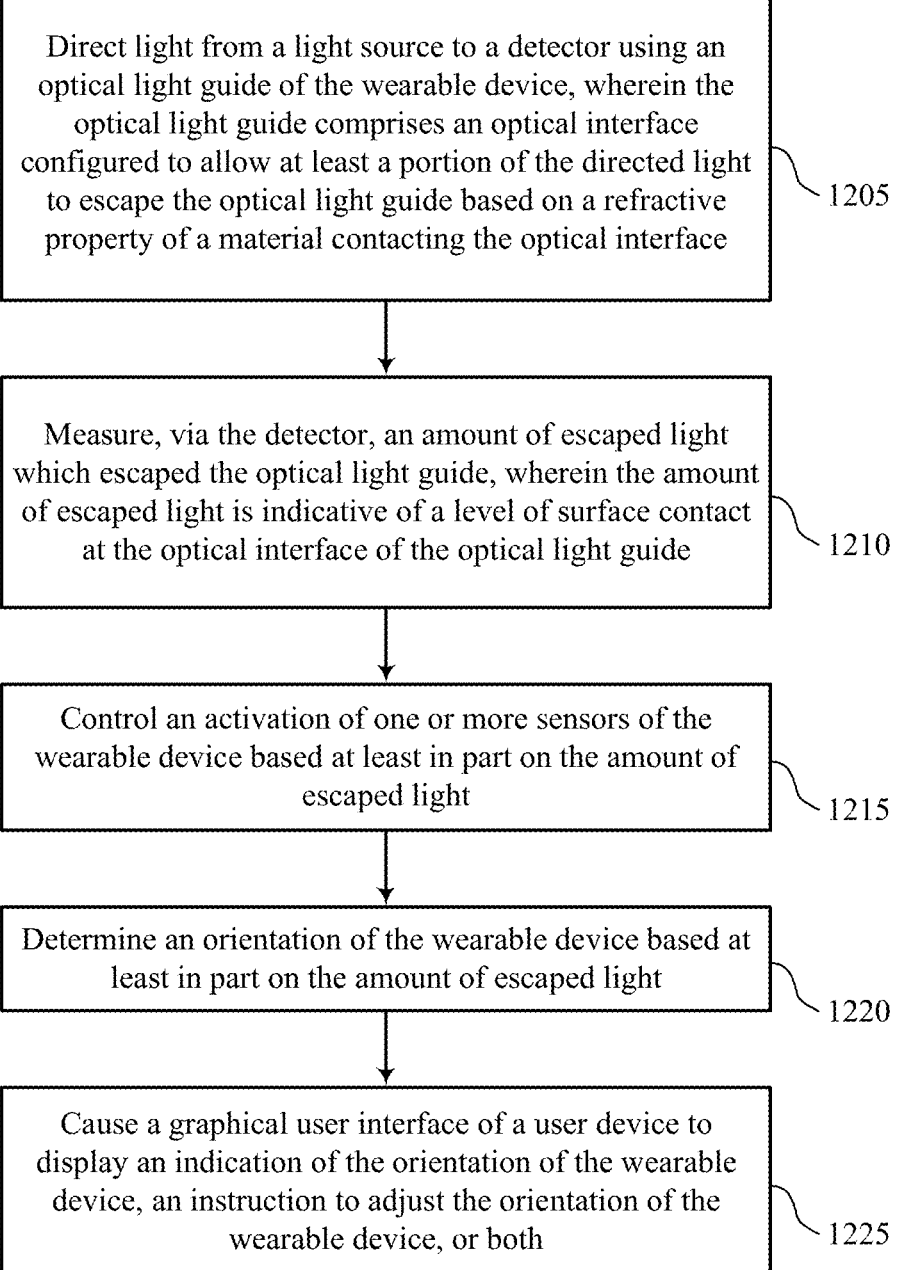

Direct light from a light source to a detector using an optical light guide of the wearable device, wherein the optical light guide comprises an optical interface configured to allow at least a portion of the directed light to escape the optical light guide based on a refractive property of a material contacting the optical interface

1205

Measure, via the detector, an amount of escaped light which escaped the optical light guide, wherein the amount of escaped light is indicative of a level of surface contact at the optical interface of the optical light guide

1210

Control an activation of one or more sensors of the wearable device based at least in part on the amount of escaped light

1215

Determine an orientation of the wearable device based at least in part on the amount of escaped light

1220

Cause a graphical user interface of a user device to display an indication of the orientation of the wearable device, an instruction to adjust the orientation of the wearable device, or both

WEARING DETECTION TECHNIQUES FOR WEARABLE DEVICES

CROSS REFERENCE

The present Application for Patent claims the benefit of U.S. Provisional Patent Application No. 63/244,233 by MÄKINEN, entitled "WEARING DETECTION TECHNIQUES FOR WEARABLE DEVICES," filed Sep. 14, 2021, assigned to the assignee hereof, and expressly incorporated by reference herein.

FIELD OF TECHNOLOGY

The following relates to wearable devices and data processing, including wearing detection techniques for wearable devices.

BACKGROUND

Some wearable devices may be configured to collect physiological data from users, including temperature data, heart rate data, and the like. However, poor contact between a user's skin and one or more sensors of a wearable device may result in inaccurate measurements.

BRIEF DESCRIPTION OF THE DRAWINGS

FIGS. 10 through 12 show flowcharts illustrating methods that support wearing detection techniques for wearable devices in accordance with aspects of the present disclosure.

DETAILED DESCRIPTION

Figure 1:
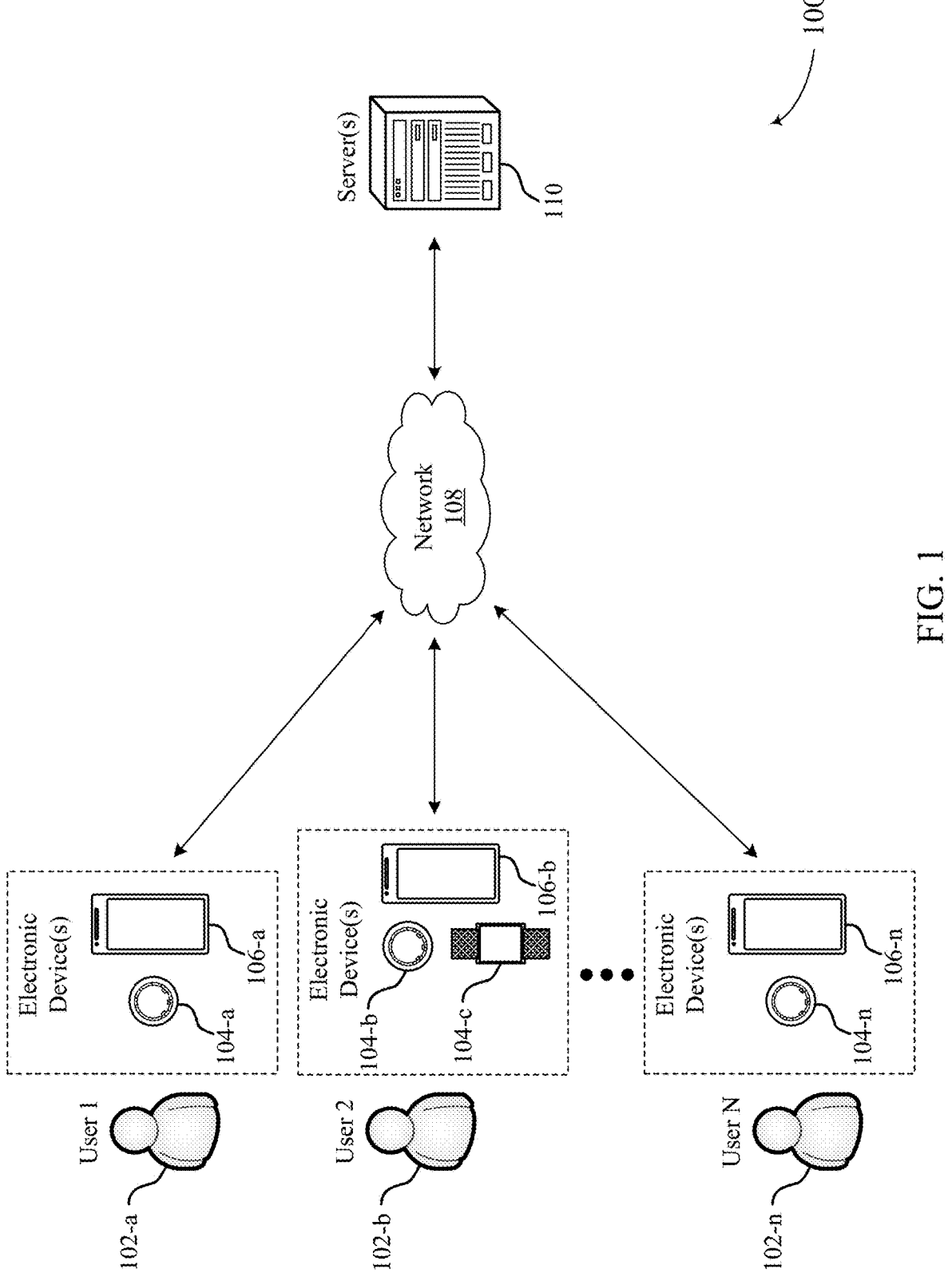
FIG. 1 illustrates an example of a system that supports wearing detection techniques for wearable devices in accordance with aspects of the present disclosure.

Some wearable devices may be configured to collect data from users associated with movement and other activities. For example, some wearable devices may be configured to continuously acquire physiological data associated with a user including temperature data, heart rate data, and the like. In order to efficiently and accurately track physiological data, a wearable device may be configured to collect data continuously while the user wears the device.

In some cases, there may be a gap between the skin of a user and a wearable device. For example, if the wearable device is a ring, pressure on the ring may create an air gap between the other side of the ring and the skin of the user due to a finger of the user being depressed against the ring. In some other examples, if the wearable device is worn on a wrist of a user, pressure on the device may create an air gap between the opposite side of the device and the skin of the user due to a wrist of the user being depressed against the wearable device. Additionally, or alternatively, the wearable device may be relatively large for a user, which may create gaps between the wearable device and the skin of the user (e.g., ill-fitting ring). The gap may align with one or more sensors of the wearable device, such as one or more light emitting diodes (LEDs), which may create new optical interfaces between the skin of the user and the sensors. The new optical interfaces may behave differently as compared to cases where there is good skin contact between the skin of the user and the sensors (e.g., may change a critical angle due to reflections, reduce perfusion index due to internal stray light, cause variations in distribution of light, and the like). In some examples, contaminants such as dirt and liquids may be positioned between the wearable device and the finger, which may further distort one or more light wavelengths emitted from the LEDs. The variation in optical interface and wavelength may cause inaccurate readings from the sensors. In some cases, the wearable device may adjust a power of the sensors, such as increasing the brightness of an LED, to account for the variation in readings, which may increase power consumption at the wearable device. Taken together, these issues with wearable devices may result in inaccurate physiological data readings, which may lead to a distorted picture of the user's overall health, as well as increased power consumption and decreased battery life.

Accordingly, techniques described herein are directed to systems and methods for determining whether a user is wearing a wearable device. More specifically, techniques described herein are directed to the use of a light guide apparatus which is configured to determine a level of skin contact at various sensors of a wearable device. By determining when a user is wearing a wearable device, as well as determining whether there is sufficient skin contact with or near sensors of a wearable device, techniques described herein may lead to more accurate physiological data measurements, and may decrease a power consumption at the wearable device, which may lead to longer battery life, among other benefits.

As described herein, a wearable device may include a light guide apparatus including one or more light sources and one or more light detectors to determine a level of skin contact between a user's skin and one or more sensors of the wearable device. In some examples, the light guide apparatus may include a contact sensing light guide in addition to the light source and the light detector. The light guide of the light guide apparatus may direct light from the light source, such as an LED, to the detector. The light guide may have a refractive property (e.g., refractive index) that allows a portion of light to escape the light guide, where the portion of light that escapes the light guide is dependent upon a refractive property (e.g., refractive index) of a material which is in contact with the light guide, such as air or a user's skin. For example, the wearable device may measure an amount of escaped light to determine a level of surface contact (e.g., skin contact) at the light guide. As such, by measuring the amount of light which escaped the light guide, techniques described herein may be used to determine whether or not a user is wearing the wearable device, and determine a level of skin contact when the user is wearing the wearable device.

In some examples, when the user is not wearing the wearable device or if there is an air gap between the wearable device and the skin of the user, the differences between refractive indexes of the light guide and the air may cause the light to stay within the light guide. Thus, the detector may receive a relatively large portion of the light. In some other examples, when the user is wearing the ring and there is skin contact between the wearable device and the user, the refractive index of the skin causes light to leach out of the light guide into the skin, so the detector may receive relatively less light (e.g., more escaped light, and less light received at the detector). In some cases, light guide apparatuses within a wearable device may be used to determine a relative orientation of the wearable device. Moreover, the wearable device may control activation of one or more LED-photodetector (PD) sensors based on the amount of escaped light (e.g., may turn off the sensors when there is no skin contact detected). Additionally, or alternatively, the wearable device may alert the user via a graphical user interface (GUI) based on the sensors losing skin contact.

Aspects of the disclosure are initially described in the context of systems supporting physiological data collection from users via wearable devices. Additional aspects of the disclosure are described in the context of wearable user device diagrams and an example GUI. Aspects of the disclosure are further illustrated by and described with reference to apparatus diagrams, system diagrams, and flow-charts that relate to wearing detection techniques for wearable devices.

FIG. 1 illustrates an example of a system 100 that supports wearing detection techniques for wearable devices in accordance with aspects of the present disclosure. The system 100 includes a plurality of electronic devices (e.g., wearable devices 104, user devices 106) which may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (here-inafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light emitting diodes (LEDs) (e.g., red LEDs, green LEDs) that emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data. In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time during that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for determining whether a user 102 is wearing a respective wearable device 104, and for determining a level of contact (e.g., skin contact) at different portions of the wearable device. In particular, techniques described herein support a wearable device 104 which includes a light guide for determining a level of surface contact at the wearable device 104, where the level of surface contact is used to control activation of one or more sensors according to a material contacting the wearable device 104.

For example, the wearable device 104 may surround a finger, wrist, ankle, or the like, of a user 102. The wearable device 104 may be displaced by a force, may shake due to external forces or gravity, may rotate, or may move in some other way to cause a gap between the skin of a user and one or more sensors on the wearable device. A light guide of the wearable device 104 may direct light from a light source, such as from an additional LED, to a detector. The light guide may allow a portion of the directed light to escape the light guide based on a refractive property of a material in contact with the light guide, such as a refractive property of air (e.g., in cases where the user 102 is not wearing the ring or in cases where there is an air gap between the skin and the light guide), a refractive property of the user's 102 skin, or a refractive property of another material in contact with the light guide (e.g., if there is contaminant between the sensor and the skin).

In general, an amount of light which escapes the light guide may be directly proportional to a level of estimated skin contact with the wearable device, where larger amounts of escaped light may be indicative of sufficient skin contact and smaller amounts of escaped light may be indicative of insufficient or no skin contact. As such, if a relatively large portion of light escapes the light guide, the wearable device 104 may determine there is skin contact with the sensors, and may continue to take measurements via the one or more sensors (e.g., heart rate measurements, oxygen saturation measurements (SpO2), temperature, sleep measurements, and the like). Comparatively, if a relatively small portion of light escapes the light guide, the wearable device 104 may determine there is air or contaminant between the sensors and skin of a user 102, and may therefore determine that the user is not wearing the wearable device 104 or determine that there is insufficient skin contact with the wearable device. As such, the wearable device 104 may pause measurements via the one or more sensors or send an alert to the user 102 (e.g., via the user device 106) for the user to wear the wearable device 104 and/or adjust an orientation of the wearable device 104 to improve skin contact.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
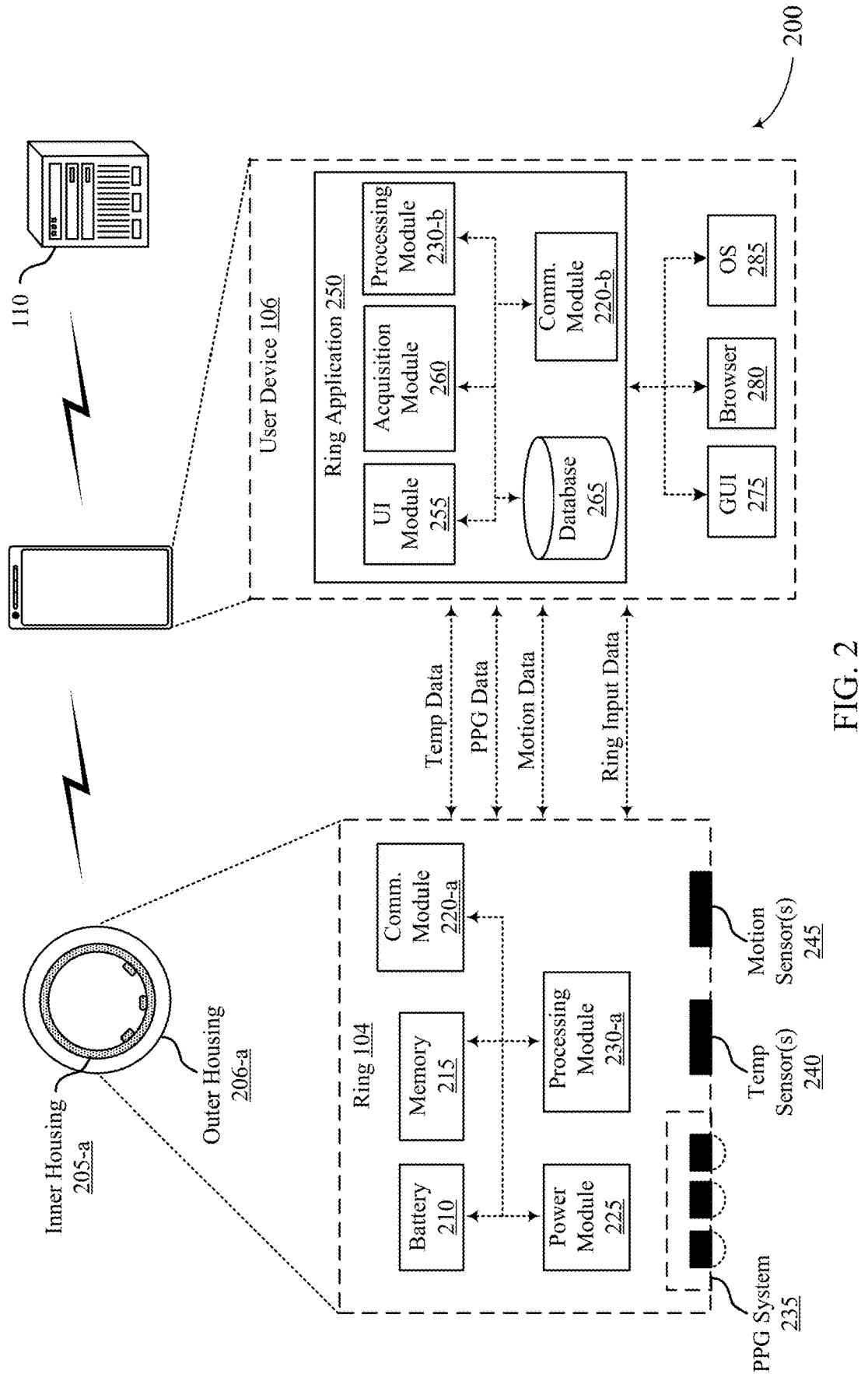
FIG. 2 illustrates an example of a system that supports wearing detection techniques for wearable devices in accordance with aspects of the present disclosure.

FIG. 2 illustrates an example of a system 200 that supports wearing detection techniques for wearable devices in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

System 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205, which may include an inner housing 205-a and an outer housing 206-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components which are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 206-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 206-b (e.g., a metal outer housing 206-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 206-b may be fabricated from one or more materials. In some implementations, the outer housing 206-b may include a metal, such as titanium, which may provide strength and abrasion resistance at a relatively light weight. The outer housing 206-b may also be fabricated from other materials, such polymers. In some implementations, the outer housing 206-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG LEDs. In some implementations, the inner housing 205-a component may be molded onto the outer housing 205-a. For example, the inner housing 205-a may include a polymer that is molded (e.g., injection molded) to fit into an outer housing 206-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-a of the ring 104 may include one or more processors (e.g., processing units), microcontrollers, digital signal processors, systems on a chip (SOCs), and/or other processing devices. The processing module 230-a communicates with the modules included in the ring 104. For example, the processing module 230-a may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-a may communicate with the memory 215. The memory 215 may include computer-readable instructions that, when executed by the processing module 230-a, cause the processing module 230-a to perform the various functions attributed to the processing module 230-a herein. In some implementations, the processing module 230-a (e.g., a microcontroller) may include additional features associated with other modules, such as communication functionality provided by the communication module 220-a (e.g., an integrated Bluetooth Low Energy transceiver) and/or additional onboard memory 215.

The communication module 220-a may include circuits that provide wireless and/or wired communication with the user device 106 (e.g., communication module 220-b of the user device 106). In some implementations, the communication modules 220-a, 220-b may include wireless communication circuits, such as Bluetooth circuits and/or Wi-Fi circuits. In some implementations, the communication modules 220-a, 220-b can include wired communication circuits, such as Universal Serial Bus (USB) communication circuits. Using the communication module 220-a, the ring 104 and the user device 106 may be configured to communicate with each other. The processing module 230-a of the ring may be configured to transmit/receive data to/from the user device 106 via the communication module 220-a. Example data may include, but is not limited to, motion data, temperature data, pulse waveforms, heart rate data, HRV data, PPG data, and status updates (e.g., charging status, battery charge level, and/or ring 104 configuration settings). The processing module 230-a of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors which may be used to collect data in addition to, or which supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-a) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-a may sample the user's temperature over time. For example, the processing module 230-a may sample the user's temperature according to a sampling rate. An example sampling rate may include one sample per second, although the processing module 230-a may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 in which the optical receiver(s) receive transmitted light that is reflected through the region of the user's finger. In some implementations, the PPG system 235 may be configured as a transmissive PPG system 235 in which the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include LEDs. The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform, which may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics (e.g., a Activity Score), and readiness metrics (e.g., a Readiness Score). In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/ systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") which may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b,* a communication module 220-*b,* and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations which require relatively low processing power and/or operations which require a relatively low latency, whereas the user device 106 may transmit the data to the servers 110 for processing operations which require relatively high processing power and/or operations which may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner which is consistent with their sleep schedules. In some cases, users may be able to selectively adjust (e.g., via the GUI) a timing of sleep days relative to calendar days so that the sleep days are aligned with the duration of time in which the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for determining whether a user is wearing a wearable device 104, and for determining a level of contact (e.g., skin contact) at a wearable device. In particular, techniques described herein support a wearable device 104, such as a wearable device 104 as described with reference to FIG. 1, which includes a light guide for determining a level of surface contact at the wearable device, where the level of surface contact is used to control activation of one or more sensors according to a material contacting the wearable device 104.

For example, the wearable device 104 may surround a finger, wrist, ankle, or the like of a user. In some cases, the wearable device 104 may not be flush with the user's skin. For instance, in some cases, a force may displace the inner housing 205-*a* of a wearable device 104 with respect to skin of a user, the wearable device 104 may shake due to external forces or gravity, the wearable device 104 may rotate with respect to the skin of the user, or may move in some other way to cause a gap between the skin of the user and one or more sensors on the wearable device 104. A light guide of the wearable device 104 may direct light from a light source, such as from a colored LED light located at inner housing 205-*a*, to a detector, which may also be located at inner housing 205-*a*. The light guide may allow a portion of the directed light to escape the light guide based on a refractive property of a material contacting the surface of the light guide. In this regard, the amount of light which escapes the light guide may be based on a type of material in contact with the light guide (e.g., air, a user's skin, or another material in contact with the sensor such as dirt, sweat, or water), as well as a level of surface contact (e.g., pressure of the contact) with the light guide.

In some examples, the light guide may be molded into the grooves of inner housing 205-*a* of the wearable device. The light guide may be constructed of a material that conducts light, such as an optically clear epoxy. That is, there may be a channel of epoxy within the inner housing 205-*a* (e.g., surrounded by metal) that serves as the light guide. The light guide may direct the light from a light source, such as a colored LED light, to a light detector. The LED light may be a blue LED light, a yellow LED light, a green LED light, or some other color LED light.

In some examples, the detector may measure an amount of light which is received from the light source via the light guide. In general, an amount of light which escapes the light guide may be directly proportional to a level of estimated skin contact with the wearable device, where larger amounts of escaped light may be indicative of sufficient skin contact and smaller amounts of escaped light may be indicative of insufficient or no skin contact. For example, if the received amount of light (e.g., received signal) is relatively strong, not much light may have escaped the light guide. Thus, there may be a material other than skin in contact with the guide or light source. Comparatively, if the received amount of light is relatively weak, light may have escaped the light guide, which may mean skin is in contact with the light source, the light guide, or both. The light guide may be strategically placed within the inner housing 205-*a* to detect whether the user has skin contact with one or more additional sensors taking physiological measurements from the user (e.g., temperature sensors, additional LED-PD sensors used for measuring heart rate, oxygen saturation, one or more sensors that a device may use to detect whether a user is asleep, or the like).

If a relatively large portion of light escapes the light guide, the wearable device 104 may determine there is skin contact with the sensors, and may continue to take measurements via the one or more sensors. If a relatively small portion of light escapes the light guide, the wearable device 104 may determine there is air or contaminant between the sensors and skin of a user, and may pause measurements via the one or more sensors or send an alert to the user. For example, the wearable device 104 may use a connection with a user device 106 to alert the user of a potential air gap between the sensors and the skin of the user. The user device 106 may display an alert message at a GUI 275 of the user device 106. The alert message may indicate for the user to reposition the ring, may alert the user of a pause in data collection, or the like, which is described in further detail with respect to FIG. 6.

Figure 3:
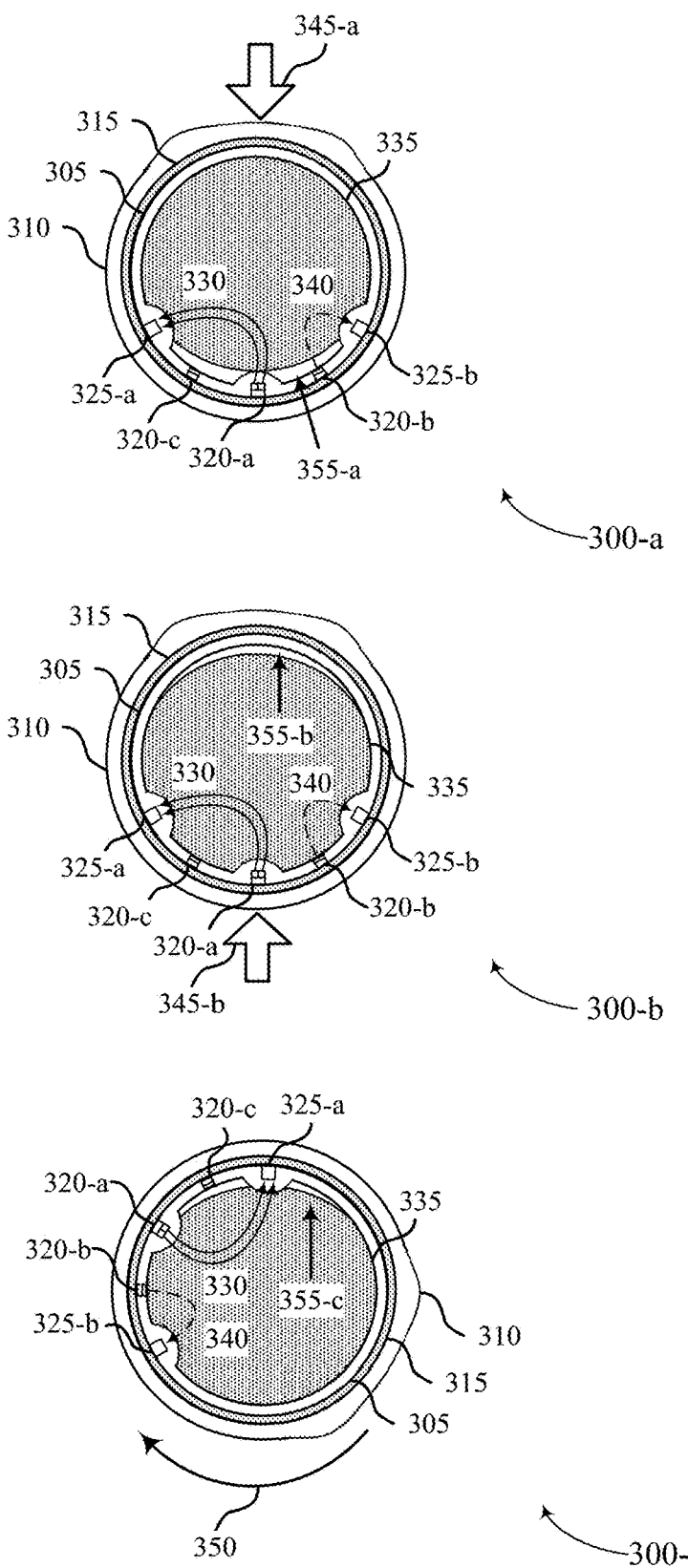
FIGS. 3 through 5 illustrate examples of wearable device diagrams that support wearing detection techniques for wearable devices in accordance with aspects of the present disclosure.

FIG. 3 illustrates an example of a wearable device diagram 300 that supports wearing detection techniques for wearable devices in accordance with aspects of the present disclosure. The wearable device diagram 300 may implement, or be implemented by, aspects of the system 100, system 200, or both. For example, wearable device diagram 300-*a*, wearable device diagram 300-*b*, and wearable device diagram 300-*c*, may illustrate examples of wearable devices 104 as described with reference to FIG. 1. Specifically, the wearable device diagrams 300-*a*, 300-*b*, and 300-*c* may illustrate different orientations of a wearable ring device on a user's finger. Although wearable device (e.g., a watch, a necklace, and the like).

The wearable device in wearable device diagram 300-*a* through wearable device diagram 300-*c* may include an inner housing 305 and an outer housing 310, which may be examples of an inner housing 205 and an outer housing 206 as described with reference to FIG. 2. In some cases, an outer opaque shell may be molded over an inner structure of the wearable device. Further, the wearable device in wearable device diagram 300-*a* through wearable device diagram 300-*c* may include an electronic substrate 315, such as a printed wiring board (PWB) or PCB. The PWB may have both flexible and rigid sections. One or more sensors may be embedded in the electronic substrate 315. For example, the electronic substrate may include one or more LEDs 320 and PDs 325. The wearable device may include LED 320-*a*, which may emit light 330 received by PD 325-*a* and/or PD 325-*a*. In this regard, the LED 320-*a* may support two optical channels for physiological data measurements: a first optical channel between the LED 320-*a* and the PD 325-*a* and a second optical channel between the LED 320-*a* and the PD 325-*b*. The wearable device may include any number of LEDs, PDs, and respective optical channels for physiological data measurements. In some cases, LED 320-*a* may be a red and infrared LED, which may emit light 330 that is scattered and absorbed by skin 335 of a user of the wearable device 300-*a*.

Similarly, the wearable device may include LED 320-*b* and LED 320-*c*. LED 320-*b* may emit light 340. LED 320-*b* and LED 320-*c* may be green LEDs, blue LEDs, or a combination thereof (e.g., one blue LED and one green LED). The light 340 may be scattered and absorbed by the skin 335 of the user, and measured via the PDs 325-*a* and/or 325-*b*. As noted previously herein, each of the LEDs 320-*b* and 320-*c* may support multiple optical channels via the respective PDs 325-*a*, 325-*b*. The PDs 325-*a*, 325-*b* may be configured to measure light from the respective LEDs 320 which is reflected by the skin and/or transmitted through the skin (e.g., reflective and/or transmissive measurements).

In some cases, the inner housing 305 may include a dome structure over the one or more LEDs 320, one or more PDs 325, or both. For example, the wearable device may include dome structures over LED 320-*a*, PD 325-*a*, and PD 325-*b* to improve contact with the skin 335. In some other cases, there may be a window for the LED 320 to emit light 330 or light 340. For example, LED 320-*b* and LED 320-*c* may have a window in inner housing 305. An optical interface may form between the inner housing 305 and the domes or the windows (e.g., with a refractive index of ~1.57) and the top layer of skin 335 (e.g., with a refractive index of ~1.55). The wearable device may use the light propagation from the LEDs 320 to the PDs 325 through tissue for physiological measurements, such as PPG and SpO2 measurements. That is, the wearable device may use light 330 from LED 320-*a*, which may include red and infrared wavelengths, to measure SpO2 and light 340 from LED 320-*b*, which may include green wavelengths, to measure PPG. Light 330 may penetrate skin 335 to a different depth than light 340.

In some cases, in addition to the scattering and absorption properties of the skin 335, the multiple interfaces between optical features and the skin 335 may determine how well the optical signal is transmitted from the LEDs 320 to the PDs 325. For example, with good skin contact and embedded LEDs 320, a relatively influential optical interface type is between the inner housing 305 and the skin 335, such as the skin outer layer, stratum corneum. The total internal reflection (TIR) critical angle may be relatively large over the optical interface (e.g., 81 degrees), and light out-coupling from the inner housing 305 may be relatively efficient (e.g., <0.1% light lost at the interface via Fresnel reflections) . Thus, total light coupling losses from LEDs 320 to skin 335 may be relatively low. The TIR is an optical phenomenon when light propagating inside optically clear material hits an interface between the material and another optical material with lower refractive index, the light may be totally reflected back into a light guide/LED 320 if the angle of incidence is large enough. The TIR critical angle may depend on the difference between refractive indices (n) of the LED/light guide material and the material on the other side of the interface as well as other factors (e.g., polarization).

In some examples, there may be three different types of interfaces to the skin 335 for the wearable device in addition to the optical paths between the LEDs 320 and the PDs 325 used for physiological measurements. For example, LED 320-*b* and LED 320-*c* may be embedded in inner housing 305 (e.g., in an optically clear epoxy material) and may emit light, such as light 340, coupled out of the LED optics through an inner housing 305 to skin 335 interface. Similarly, LED 320-*a* may be under a dome (e.g., made of epoxy) and may emit light 330 coupled out of LED optics through the inner housing 305 to skin 335 interface. LED 320-*a* may be flush with the surface of the inner housing 305, such that the skin may make direct contact with LED 320-*a*. Further, light propagating inside the skin 335 (e.g., finger tissue) may be coupled to the PD optics through skin 335 to inner housing 305 interface.

In some examples, the wearable devices may be subjected to a force 345 or an acceleration 350, causing a gap 355 between skin of a user and one or more sensors at the wearable device. For example, a force 345-*a* or force 345-*b* may create gap 355-*a* or gap 355-*b*, respectively. Force 345-*a* may be applied to the top of the wearable device (e.g., the top of the wrist or finger if the wearable device is a watch or ring), which may cause a depression of the skin 335, creating gap 355-*a* opposite force 345-*a*, such as at the bottom of the wearable device. Similarly, force 345-*b* may be applied to the bottom of the wearable device (e.g., the palm of the finger or the inside of the wrist), which may cause a depression of the skin 335, creating gap 355-*b* opposite force 345-*b*, such as at the top of the wearable device. If the forces are relatively small, and the gaps 355 are therefore also relatively small (e.g., some skin contact is lost to inner housing 305), the wearable device may compensate for variation in optics to maximize signal quality.

However, if the forces 345 are large enough to create a relatively large gap 355, loss in contact for the optics (e.g., LEDs 320 and PDs 325) may cause the optical interfaces to behave differently as compared to cases with sufficient contact at the wearable device. For example, the wearable device may increase the power level of the LEDs 320 to compensate for variation in signal strength from received light at PDs 325, which may increase power consumption at the wearable device. An air gap 355 (e.g., with refractive index of ~1.00) between the skin 335 and the inner housing 305 may disturb the optical signal path as light may be coupled to the skin 335 through two interfaces (e.g., the interface between the inner housing 305 and the air and the interface between the air and the skin 335). Additionally, or alternatively, liquid or other contaminants may be trapped between the skin 335 and the inner housing 305. The contaminants may dampen or absorb the optical signals. Further, the difference between refractive indexes and contaminant layer absorption spectra may determine how different signal paths/channels may be affected (e.g., causing increased variability in signal strength).

With relatively sufficient skin contact, total light coupling losses from LEDs 320 to skin 335 may be relatively low, but there may still be optical losses due to a relatively high TIR critical angle (e.g., of greater than 81 degrees) and aperture clipping. However, if there is a gap 355 between the ring optics (e.g., embedded in inner housing 305) and the skin 335, the first optical interface is now between the inner housing (e.g., n~1.57) and air (n~1.00), and the TIR critical angle may be relatively low (e.g., ~40 degrees), which may cause losses to light coupled from LED optics. The two interfaces between the inner housing 305, the gap 355, and the skin 335, may cause an additional loss of light (e.g., ~9%) through Fresnel reflections. Changes in the optical interfaces may also alter the angular and spatial distributions of light.

Domes on top of the LEDs 320, such as on top of LED 320-a, may create steeper light incidence angles in the inner housing 305 and the skin 335 or gap 355 interface. The domes also protrude inside relatively elastic skin 335 improving contact. However, they may not be sufficiently large to solve disturbance to the in-coupled signal. Thus, any changes in the amount of light coupled into the skin 335 may be compensated by controllers or drive electronics of the wearable device, causing additional losses in battery life as well as interruptions and inaccuracy to physiological measurements (e.g., PPG and SpO2 measurements). SpO2 measurements may be especially vulnerable to losses of in-coupled light and disturbance, due to the oxygen saturation levels of blood being calculated as a ratio of two signals measured with two different wavelength LEDs 320. As the two light propagation paths are both spatially and angularly different from each other, any changes to either of the signal paths may cause measurement inaccuracy.

Motion artifacts, such as forces 345 and acceleration 350, may result in constant adjustments and power increase for the electronics of the wearable device. In some cases, the forces 345 may be external forces, such as pressure from an object, or may be due to gravity (e.g., if the wearable device is too large for the user or is being shaken or moved aggressively during activity or otherwise). The forces 345 may push the optics (e.g., LEDs 320 and PDs 325) away from contact with the skin 335, and the interfaces may change rapidly, which may cause the constant adjustments. If the fit of the wearable device is incorrect (e.g., the wearable device is too large), the signals from the optics may be weak or non-existent. The fit may change depending on the hydration level of the user, as well as natural swelling due to temperature, and the like. Additionally, or alternatively, the acceleration 350 may be a rotation of the wearable device, which may cause disruption to the signal from the optics (e.g., LEDs 320 and PDs 325). Rotation may cause loss of optical contact due to a non-circular shape of the finger 335 as well as unfavorable orientation of the skin internal structure (e.g., tissue and bone of a finger). For example, the acceleration 350 may cause a gap 355-c between the inner housing 305 and the skin 335.

In some examples, the wearable device may include one or more light guides, light sources, and detectors that may allow the wearable device to determine whether a user is wearing the wearable device, and/or to determine a level of skin contact at various portions of the wearable device. In particular, the wearable device may include a light guide apparatus which is configured to determine when a gap 355 exists. For example, the wearable device may direct light from a light source to a detector (e.g., a PD 325) using one or more optical light guides. The detector of the wearable device may measure the amount of light escaped from the optical light guide, which the wearable device may use to determine when the skin 335 is in contact with the optical light guide. If the skin 335 leaves contact with the optical light guide, the measurements may increase (e.g., more light may be guided to the detector by the light guide), and the wearable device may control activation of one or more sensors (e.g., LEDs 320 for physiological measurements) based on the skin 335 leaving contact with the optical light guide. In other words, in cases where the light guide apparatus determines that there is insufficient skin contact, the wearable device may deactivate sensors of the wearable device accordingly. The wearable device may alert a user via a GUI at a user device of the measurements, which is described in further detail with respect to FIG. 6.

Figure 4:
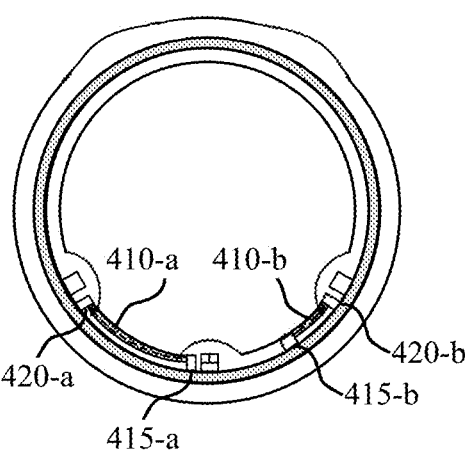
Figure 4:
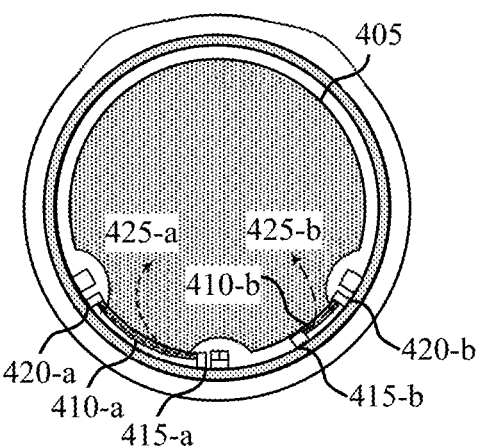

FIG. 4 illustrates an example of a wearable device diagram 400 that supports wearing detection techniques for wearable devices in accordance with aspects of the present disclosure. The wearable device diagram 400 may be implemented, or be implemented by, aspects of the system 100, system 200, wearable device diagram 300, or a combination thereof. For example, wearable device diagram 400-a and wearable device diagram 400-b may illustrate examples of wearable devices 104 as described with reference to FIGS. 1-2. Although the wearable devices are illustrated as rings in FIG. 4, aspects and components of the wearable devices illustrated in FIG. 4 may be implemented in any type of wearable device (e.g., a watch, a bracelet, a necklace, and the like).

In some examples, the wearable device may include an inner housing and an outer housing, which may be examples of an inner housing 205, inner housing 305, outer housing 206, and outer housing 310 as described with reference to FIGS. 2 and 3. One or more sensors may be embedded in the inner housing, such as one or more LEDs and PDs for collecting physiological measurements. In some examples, an external force or rotation may cause a gap to form between the sensors and skin 405 of a user, as described with reference to FIG. 3. The gap may cause inaccurate or inefficient measurements, which may cause relatively high battery consumption at the wearable device.

In some cases, the wearable device may include one or more light guide apparatuses that may allow the wearable device to determine whether the wearable device is being worn, and for determining a level of contact (e.g., skin contact) at the wearable device (e.g., determining whether a gap between the user's skin and the sensors of the wearable device exists). In some aspects, each light guide apparatus may include an optical light guide 410, one or more light sources 415, and one or more detectors 420.

For example, the wearable device may include light guide 410-a and light guide 410-b. The light guides 410 may direct light from a light source 415 to a detector (e.g., a PD 325 as described with reference to FIG. 3). Light guide 410-a may guide light from light source 415-a to detector 420-a, while light guide 410-b may guide light from light source 415-b to detector 420-b. In some examples, the light guides may be contact sensing light guides which are configured to "leach" light (e.g., allow light to escape the optical light guides 410) based on optical properties of a material in physical contact with the respective optical light guides 410. In particular, when skin 405 is not in contact with the inner housing/optical light guide 410, light goes directly from the light source 415 to the detector 420 via the optical light guide 410 (e.g., with relatively little escaped light and loss in signal strength due to the interface between air and the light source 415).

In some cases, the light sources 415 of the light guide apparatuses may be colored LEDs, such as blue LEDs, green LEDs, yellow LEDs, or a combination thereof. Blue light (e.g., light from blue LEDs) may exhibit less skin penetration as compared to other wavelengths of light. As such, the use of blue LEDs for the light sources 415 of the light guide apparatuses may minimize potential interference of physiological measurements performed by the wearable device. Additionally, or alternatively, the light sources 415 of the light guide apparatuses may include micro LEDs (μLEDs) or laser diodes (LDs).

The wearable device may measure the amount of light escaped from the light guide 410 via a detector 420, which the wearable device may use to determine when the skin 405 is in contact with the optical light guide. In general, an amount of light which escapes the optical light guide 410 may be based on a refractive property of a material which is in physical contact with each respective optical light guide 410. In some cases, an amount of light which escapes each optical light guide 410 may be directly proportional to a level of estimated skin contact with the wearable device. In particular, when a user is not wearing the wearable device, or in cases where there is little or no skin contact with light guide 410, air may be in physical contact with the light guide and little or no light may escape the light guide 410, as shown in wearable device diagram 400-*a*. Comparatively, in cases where there is sufficient skin contact with light guide 410, skin 405 may be in physical contact with the light guide 410 and larger quantities of light may escape the light guide 410, as shown in wearable device diagram 400-*b*.

For example, if the skin 405 leaves contact with light guide 410-*a*, light guide 410-*b*, or both, the measurements at detector 420-*a* and detector 420-*b*, respectively, may increase (e.g., more light may be reflected back to the detector by the light guide 410, with little light escaping the light guide 410). If the skin 405 leaves contact with the light guide 410, such as when the user is not wearing the wearable device or if there is insufficient skin contact, the wearable device may control activation of one or more sensors (e.g., deactivate LEDs and PDs for physiological measurements) to reduce power consumption of the wearable device. If the skin 405 remains in contact with light guide 410-*a*, light guide 410-*b*, or both, the measurements at detector 420-*a* and detector 420-*b*, the refractive properties of the skin 405 may cause larger amounts of light to escape the light guide 410, resulting in relatively low signal strengths measured at the detectors 420. In other words, light 425 may escape through the skin due to the interface between the light sources 415 and the skin 405 (e.g., respective refractive indexes). That is, light 425-*a* from light source 415-*a* and light 425-*b* from light source 415-*b* may be absorbed or scattered by the skin 405. With skin contact (e.g., the stratum corneum layer of skin 405), some optical signal may be coupled out from the light guides 410, and the detectors 420 may measure the change.

In some aspects, light sources for the light guide apparatuses may include dedicated light sources which are separate from other light sources used for performing physiological data measurements. For example, the light source 415-*a* may include a dedicated light source 415-*a* which is separate from green/red LEDs and infrared light sources of the wearable device. Additionally or alternately, one or more light sources which are used for performing physiological data measurements may be used as a light source for a light guide apparatus. For example, the light source 415-*b* may include a green LED which is configured for performing physiological data measurements, and for directing light down the light guide 410-*b*.

Figure 5:
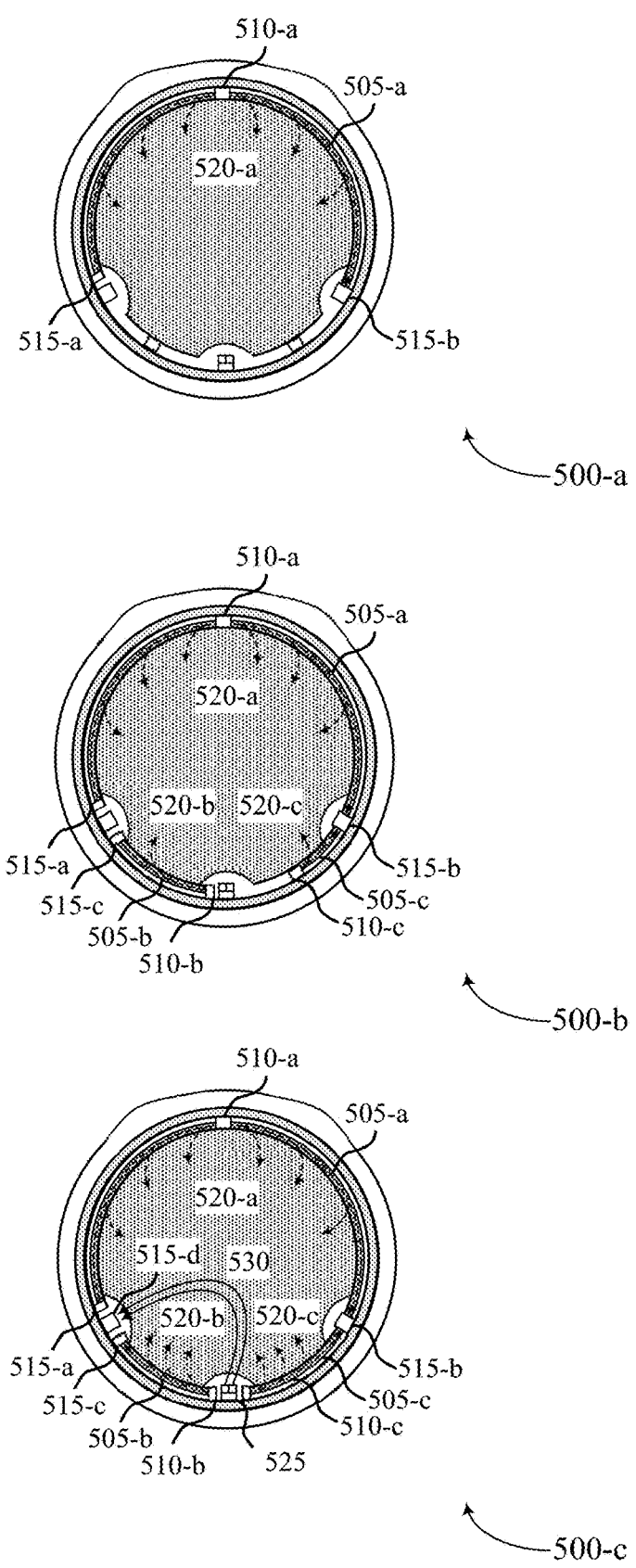

FIG. 5 illustrates an example of a wearable device diagram 500 that supports wearing detection techniques for wearable devices in accordance with aspects of the present disclosure. The wearable device diagram 500 may be implemented, or be implemented by, aspects of the system 100, system 200, wearable device diagram 300, wearable device diagram 400, or a combination thereof. For example, wearable device diagram 500-*a*, wearable device diagram 500-*b*, and wearable device diagram 500-*c* may illustrate examples of wearable devices 104 as described with reference to FIGS. 1-4. Although the wearable devices are illustrated as rings in FIG. 5, aspects and components of the wearable devices illustrated in FIG. 5 may be implemented in any type of wearable device (e.g., a watch, a bracelet, a necklace, and the like).

In some examples, the wearable device may include an inner housing and an outer housing, which may be examples of an inner housing 205, inner housing 305, outer housing 206, and outer housing 310 as described with reference to FIGS. 2 and 3. One or more sensors may be embedded in the inner housing, such as one or more LEDs for collecting physiological measurements. In some examples, an external force or rotation may cause a gap to form between the sensors and skin of a user, as described with reference to FIG. 3. The gap may cause inaccurate or inefficient measurements, which may cause relatively high battery consumption at the wearable device.

In some cases, the wearable device may include one or more light guide apparatuses that may allow the wearable device to determine whether the wearable device is being worn, and for determining a level of contact (e.g., skin contact) at the wearable device (e.g., determining whether a gap between the user's skin and the sensors of the wearable device exists). Each light guide apparatus may include one or more optical light guides 505, one or more light sources 510, and one or more detectors 515. As noted previously herein, an amount of light which escapes the respective optical light guide 505 may be based on a refractive property of a material which is in physical contact with each respective optical light guide 505. In some cases, an amount of light which escapes each optical light guide 505 may be directly proportional to a level of estimated skin contact with the wearable device.

For example, a wearable device as illustrated in wearable device diagram 500-*a*, wearable device diagram 500-*b*, wearable device diagram 500-*c*, or a combination thereof, may include light guide 505-*a*. The light guide 505-*a* may span a portion of the inner housing of the wearable device, where the portion may be any size (e.g., any length). In some examples, where a light emitting device (e.g., an LED) and a photodetector are located adjacent to each other (e.g., relatively close to each other), the light guide 505-*a* may be relatively short and just comprise the epoxy (or other similar material) between the light emitting device and the photodetector. In some examples, the light guide 505-*a* may span the top portion of the inner housing of the wearable device. In some examples, with relatively longer contact sensing light guides 505, the change to signal strength may be relatively larger. Light source 510-*a*, which may be a green LED, may emit light 520-*a*, such that light 520-*a* may be guided along light guide 505-*a* to detector 515-*a* and detector 515-*b*, which may be examples of PDs. In some cases, detector 515-*a*, detector 515-*b*, or both may detect light emitted from one or more light sources 510, such as light source 510-*a* and one or more additional light sources 510 used for physiological measurements. In some other cases, detector 515-*a*, detector 515-*b*, or both may be specific to light source 510-*a*.

Similarly, a wearable device as illustrated in wearable device diagram 500-*b* and wearable device diagram 500-*c* may include one or more additional light guides 505, such as light guide 505-*b* and light guide 505-*c*. Light guide 505-*b* may guide light 520-*b* from light source 510-*b* to detector 515-*c* or detector 515-*a*. Light guide 505-*c* may guide light 520-*c* from light source 510-*c* to detector 515-*b*. That is, a single LED or PD may be used together with multiple light guides 505 to save cost and space. In some examples, light source 510-*b*, light source 510-*c*, or both may be colored LEDs used for detecting whether there is skin contact at one or more sensors of the wearable device, may be used for performing physiological measurements, or both.

With several light guides 505 and optoelectronic components it may be possible to determine differing levels of skin contact along different portions (e.g., radial positions relative to an axis) of the inner housing (e.g., inner circumference) of the wearable device. For example, if the skin of a user separates from the inner housing anywhere along light guide 505-*a*, light guide 505-*b*, light guide 505-*c*, or a combination thereof, the wearable device will not only know that the skin contact is not good along the entire inner housing, but will also know where the gap in skin contact occurs. Thus, the contact sensing light guides 505 may help to determine which sensors to use (e.g., PPG sensors). For example, as illustrated in wearable device diagram 500-*c*, if a light guide signal is weaker at detector 515-*b* that at detector 515-*a*, detector 515-*c*, or both (e.g., weaker on one side of the wearable device than on the other), the wearable device may use a sensor 525 (e.g., a PPG sensor) to emit light 530 to a detector 515-*d* close to detector 515-*a* and detector 515-*c*.

In other words, the use of multiple light guide apparatuses and/or optical light guides 505 may enable the wearable device to determine portions of the wearable device which exhibit sufficient skin contact for good physiological data measurement, and which portions of the wearable device exhibit insufficient skin contact for physiological data measurement. In this regard, the wearable device may selectively activate and deactivate sensors on the wearable device based on an estimated level of skin contact proximate to the respective sensors. For example, the wearable device may activate a first sensor based on a level of surface contact around the first sensor satisfying a threshold level of surface contact, and may deactivate a second sensor based on a level of surface contact around the second sensor failing to satisfy the threshold level of surface contact. By measuring the signals from the light guides 505 (e.g., at detectors 515), it may be possible to use LED and PD pairs that have sufficient optical paths during rapid motion and reduce battery consumption. In some cases, the light guides 505 may include the light source 510, such as by including a filter and an LED.

In some cases, if an RGB LED is used together with a light guide 505, the wearable device may be able to perform spectral analysis based on a user. That is, multiple wavelengths of light may be used within an optical light guide 505 for performing spectral analysis procedures, which may be used for guiding PPG wavelength selection. For example, referring to wearable device diagram 500-*c*, multiple wavelengths of light (e.g., light 520-*a*, light 520-*b*, light 520-*c*) may be directed through the light guides 505-*a*, 505-*b*, where the different wavelengths of light 520 may be coupled out of the light guides 505-*a*, 505-*b* differently based on a material in contact with the light guides 505 that exhibits spectral differences in refractive index or absorptance. In other words, different quantities/proportions of the respective wavelengths of light 520 may escape the optical light guides 505 based on optical properties of a material in contact with the respective light guides 505. In some examples, spectral analysis procedures performed by the wearable device may provide for the wearable device to alert the user of one or more medical conditions, such as diabetes.

Disturbances caused by poor skin contact may be detected with components used for PPG measurement. In some cases, in addition to skin contact, changes in finger internal structure may cause changes to the physiological measurements. Thus, by using lower energy emitter components (e.g., μLEDs or LDs) with the light guides 505, relative reduced power consumption may be achieved when compared to the use of current PPG or SpO2 sensor components. In some cases, the light sources 510 may be blue LEDs, which may be different color LEDs than the LEDs used for physiological measurements. Using blue LEDs, such as blue μLEDs, may allow the wearable device to separate the signals from the signals used for physiological measurements (e.g., PPG or SpO2 signals) with the help of spectral filtering if the contact sensing creates additional noise. Further, blue light may have relatively shallow skin penetration depth when compared with green, red, IR, and the like making the light more localized to skin areas. The light guides 505 may provide for user interface functions or methods by rotating the wearable device according to a detection from the light guide 505, algorithms for analyzing the data from the physiological measurements as well as additional system descriptions, and optical measurement functions for spectral or chemical analysis with very sensitive optical features.

In some examples, the wearable device may collect data regarding gaps in skin contact at one or more sensors. The wearable device may use the data to detect a pattern of loss of skin contact, such that the wearable device may predict when the sensors may lose contact with the skin of a user. The wearable device may activate or deactivate one or more sensors according to the pattern.

Figure 6:
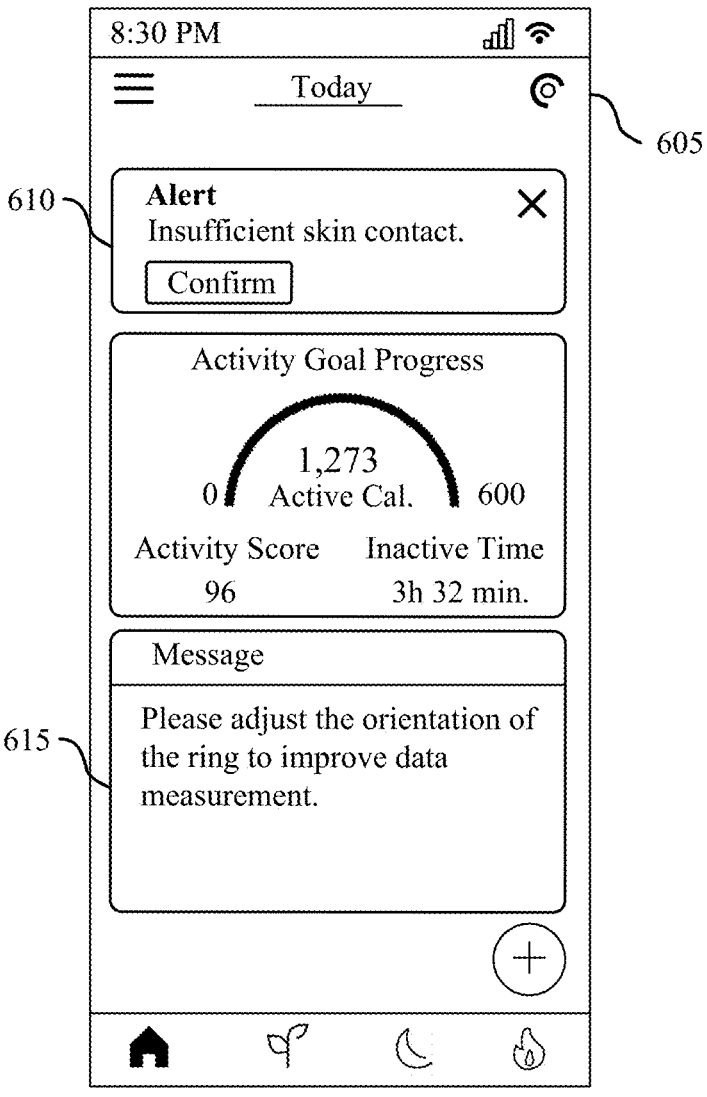
FIG. 6 illustrates an example of a graphical user interface (GUI) that supports wearing detection techniques for wearable devices in accordance with aspects of the present disclosure.

FIG. 6 illustrates an example of a GUI 600 that supports wearing detection techniques for wearable devices in accordance with aspects of the present disclosure. The wearable device diagram 500 may implement, or be implemented by, aspects of the system 100, system 200, wearable device diagram 300, wearable device diagram 400, or a combination thereof. For example, wearable device diagram 500-*a*, wearable device diagram 500-*b*, and wearable device diagram 500-*c* may illustrate examples of wearable devices 104 as described with reference to FIG. 1. Although the wearable devices are illustrated as rings in FIG. 5, they may be any example of a wearable device (e.g., a watch, a necklace, and the like).

In some examples, a wearable device may detect that a user is not wearing the wearable device and/or may detect a gap between one or more sensors in the inner housing of the wearable device and the skin of a user, as described with respect to FIGS. 2 through 5. Once the wearable device detects poor skin contact, the wearable device may send an indication of the poor skin contact to a user device 605 of the user. The indication may be an alert 610 or other notification for the user to perform an action. For example, the alert 610 may indicate for the user to adjust the position or placement of the wearable device, clean the wearable device, exchange the wearable device for a different size, or the like to reduce or eliminate the gap. In some cases, the display may prompt the user to acknowledge the message regarding the detected gap, such as by pressing a "confirm" or "dismiss" button. In some examples, the GUI 600 may display an indication of the orientation of the wearable device, an instruction to adjust the orientation of the wearable device, or both. For example, the GUI 600 may display an indication of the orientation of a ring with respect to a finger.

In some cases, the user device 605 may display a message 615 with additional details regarding the location of the loss of skin contact, one or more results of a spectral analysis, or the like based on data from one or more light guides. For example, as shown in FIG. 6, the user device 605 may display a message 615 instructing the user to adjust an orientation of the ring to improve data measurement. The wearable device may control activation of one or more sensors of the wearable device based on whether the user acknowledges the message 615 and adjusts the position of the wearable device according to the amount of escaped light. For example, the wearable device may activate the sensors based on a level of surface contact satisfying a threshold level of surface contact, deactivate the sensors based on the level of surface contact being below a threshold level of surface contact (e.g., failing to satisfy), or the like.

In some cases, a user device 605 may use the contact sensing system as a UI for controlling the functions of the wearable device or associated software on external devices. For example, intentional rotation of the ring performed by a user could control a scrolling action on a mobile device application display, such as GUI 600, or a series of taps on a specific side of the ring could activate a higher frequency PPG measurement of the ring for an exercise session. That is, the methods described herein for measuring a level of skin contact at a wearable device may be used to trigger one or more applications or functions at user device 605.

Figure 7:
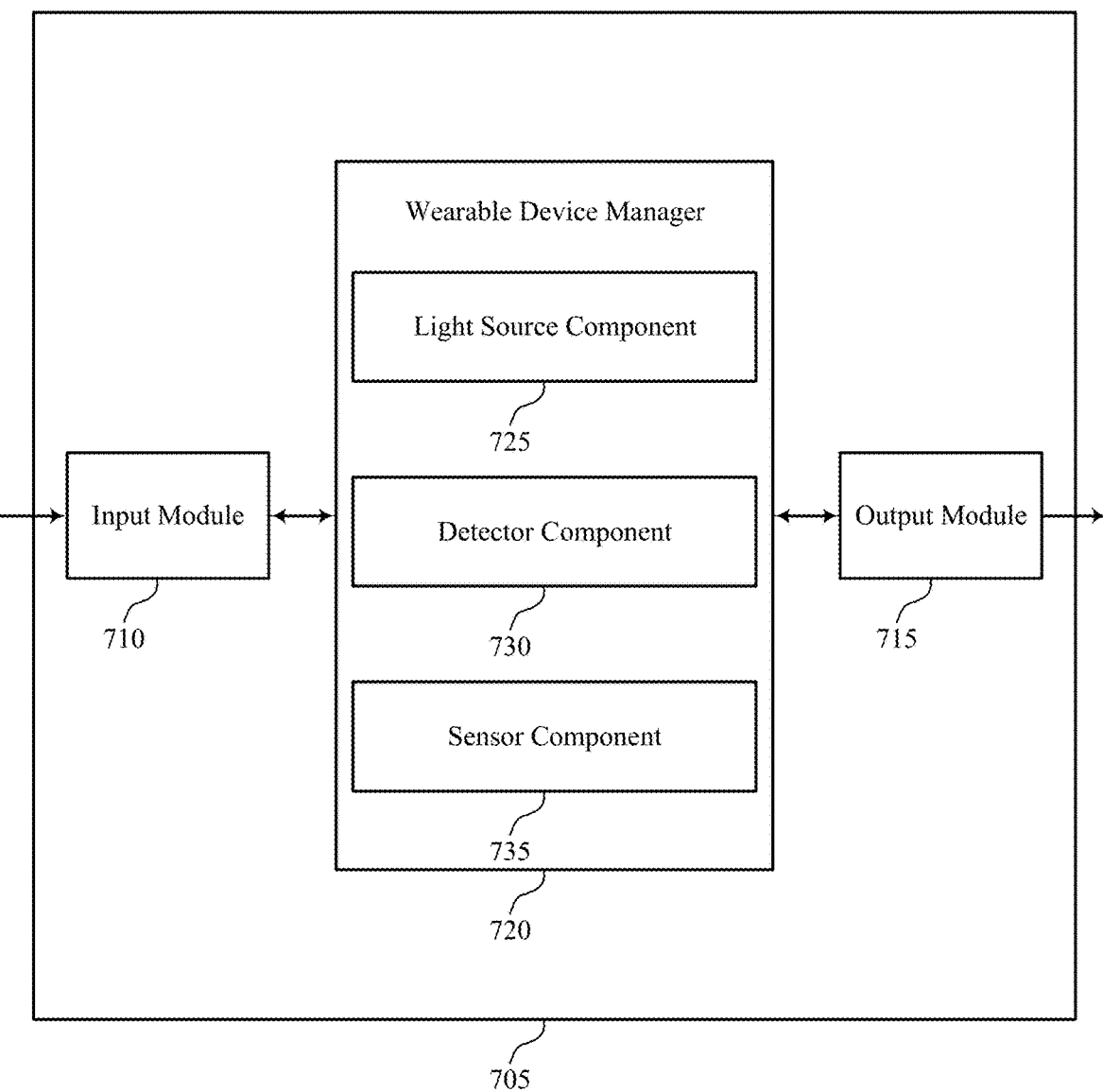
FIG. 7 shows a block diagram of an apparatus that supports wearing detection techniques for wearable devices in accordance with aspects of the present disclosure.

FIG. 7 shows a block diagram 700 of a device 705 that supports wearing detection techniques for wearable devices in accordance with aspects of the present disclosure. The device 705 may include an input module 710, an output module 715, and a wearable device manager 720. The device 705 may also include a processor. Each of these components may be in communication with one another (e.g., via one or more buses).

For example, the wearable device manager 720 may include a light source component 725, a detector component 730, a sensor component 735, or any combination thereof. In some examples, the wearable device manager 720, or various components thereof, may be configured to perform various operations (e.g., receiving, monitoring, transmitting) using or otherwise in cooperation with the input module 710, the output module 715, or both. For example, the wearable device manager 720 may receive information from the input module 710, send information to the output module 715, or be integrated in combination with the input module 710, the output module 715, or both to receive information, transmit information, or perform various other operations as described herein.

The wearable device manager 720 may support detecting contact with a wearable device in accordance with examples as disclosed herein. The light source component 725 may be configured as or otherwise support a means for directing light from a light source to a detector using an optical light guide of the wearable device, wherein the optical light guide comprises an optical interface configured to allow at least a portion of the directed light to escape the optical light guide based on a refractive property of a material contacting the optical interface. The detector component 730 may be configured as or otherwise support a means for measuring, via the detector, an amount of escaped light which escaped the optical light guide, wherein the amount of escaped light is indicative of a level of surface contact at the optical interface of the optical light guide. The sensor component 735 may be configured as or otherwise support a means for controlling an activation of one or more sensors of the wearable device based at least in part on the amount of escaped light.

The input module 710 may provide a means for receiving information such as packets, user data, control information, or any combination thereof associated with various information channels (e.g., control channels, data channels, information channels related to illness detection techniques). Information may be passed on to other components of the device 705. The input module 710 may utilize a single antenna or a set of multiple antennas.

The output module 715 may provide a means for transmitting signals generated by other components of the device 705. For example, the output module 715 may transmit information such as packets, user data, control information, or any combination thereof associated with various information channels (e.g., control channels, data channels, information channels related to illness detection techniques). In some examples, the output module 715 may be co-located with the input module 710 in a transceiver module. The output module 715 may utilize a single antenna or a set of multiple antennas.

For example, the wearable application 720 may include, or any combination thereof. In some examples, the wearable application 720, or various components thereof, may be configured to perform various operations (e.g., receiving, monitoring, transmitting) using or otherwise in cooperation with the input module 710, the output module 715, or both. For example, the wearable application 720 may receive information from the input module 710, send information to the output module 715, or be integrated in combination with the input module 710, the output module 715, or both to receive information, transmit information, or perform various other operations as described herein.

Figure 8:
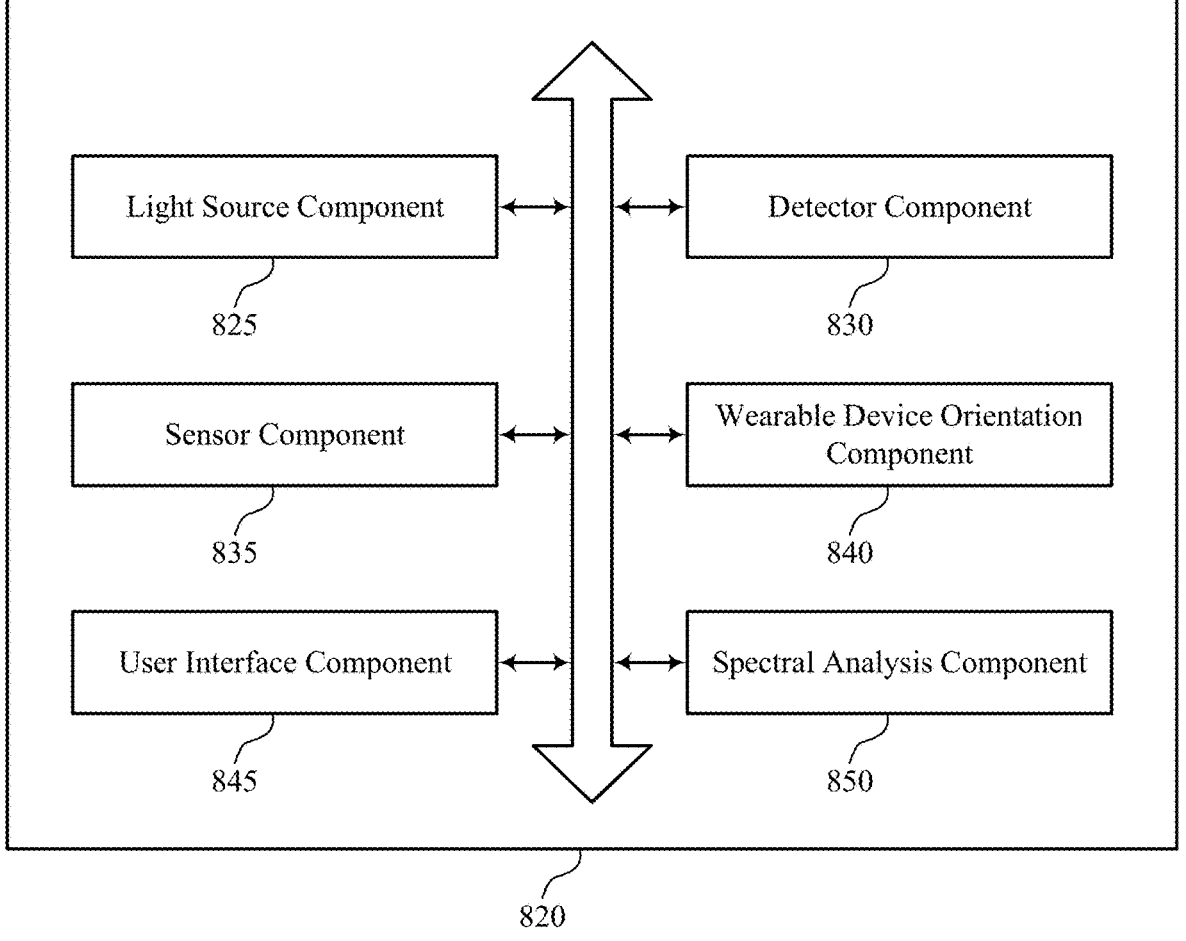
FIG. 8 shows a block diagram of a wearable device manager that supports wearing detection techniques for wearable devices in accordance with aspects of the present disclosure.

FIG. 8 shows a block diagram 800 of a wearable device manager 820 that supports wearing detection techniques for wearable devices in accordance with aspects of the present disclosure. The wearable device manager 820 may be an example of aspects of a wearable device manager or a wearable device manager 720, or both, as described herein. The wearable device manager 820, or various components thereof, may be an example of means for performing various aspects of wearing detection techniques for wearable devices as described herein. For example, the wearable device manager 820 may include a light source component 825, a detector component 830, a sensor component 835, a wearable device orientation component 840, a user interface component 845, a spectral analysis component 850, or any combination thereof. Each of these components may communicate, directly or indirectly, with one another (e.g., via one or more buses).

The wearable device manager 820 may support detecting contact with a wearable device in accordance with examples as disclosed herein. The light source component 825 may be configured as or otherwise support a means for directing light from a light source to a detector using an optical light guide of the wearable device, wherein the optical light guide comprises an optical interface configured to allow at least a portion of the directed light to escape the optical light guide based on a refractive property of a material contacting the optical interface. The detector component 830 may be configured as or otherwise support a means for measuring, via the detector, an amount of escaped light which escaped the optical light guide, wherein the amount of escaped light is indicative of a level of surface contact at the optical interface of the optical light guide. The sensor component 835 may be configured as or otherwise support a means for controlling an activation of one or more sensors of the wearable device based at least in part on the amount of escaped light.

In some examples, to support controlling the activation of one or more sensors, the sensor component 835 may be configured as or otherwise support a means for activating the one or more sensors of the wearable device based at least in part on the level of surface contact associated with the amount of escaped light satisfying a threshold level of surface contact. In some examples, to support controlling the activation of one or more sensors, the sensor component 835 may be configured as or otherwise support a means for deactivating the one or more sensors of the wearable device based at least in part on the level of surface contact associated with the amount of escaped light failing to satisfy the threshold level of surface contact.

In some examples, the light source component 825 may be configured as or otherwise support a means for directing additional light from an additional light source to an additional detector using an additional optical light guide of the wearable device, wherein the additional optical light guide comprises an additional optical interface. In some examples, the detector component 830 may be configured as or otherwise support a means for measuring, via the additional detector, an additional amount of escaped light which escaped the additional optical light guide, wherein the additional amount of escaped light is indicative of an additional level of surface contact at the additional optical interface of the additional optical light guide. In some examples, the sensor component 835 may be configured as or otherwise support a means for controlling the activation of one or more sensors of the wearable device based at least in part on the amount of escaped light, the additional amount of escaped light, or both.

In some examples, to support controlling the activation of the one or more sensors, the sensor component 835 may be configured as or otherwise support a means for controlling a first activation of a first subset of the one or more sensors of the wearable device based at least in part on the amount of escaped light. In some examples, to support controlling the activation of the one or more sensors, the sensor component 835 may be configured as or otherwise support a means for controlling a second activation of a second subset of the one or more sensors of the wearable device based at least in part on the additional amount of escaped light.

In some examples, the wearable device orientation component 840 may be configured as or otherwise support a means for determining an orientation of the wearable device based at least in part on the amount of escaped light. In some examples, the user interface component 845 may be configured as or otherwise support a means for causing a graphical user interface of a user device to display an indication of the orientation of the wearable device, an instruction to adjust the orientation of the wearable device, or both.

In some examples, the optical interface is configured to allow at least a portion of the directed light to escape the optical light guide based on a difference between the refractive property of the material and an additional refractive property of the optical light guide.

In some examples, the directed light comprises a plurality of wavelengths, and the detector component 830 may be configured as or otherwise support a means for measuring, via the detector, a plurality of amounts of escaped light which escaped the optical light guide corresponding to the plurality of wavelengths. In some examples, the directed light comprises a plurality of wavelengths, and the spectral analysis component 850 may be configured as or otherwise support a means for performing one or more spectral analysis operations based at least in part on the plurality of amounts of escaped light.

Figure 9:
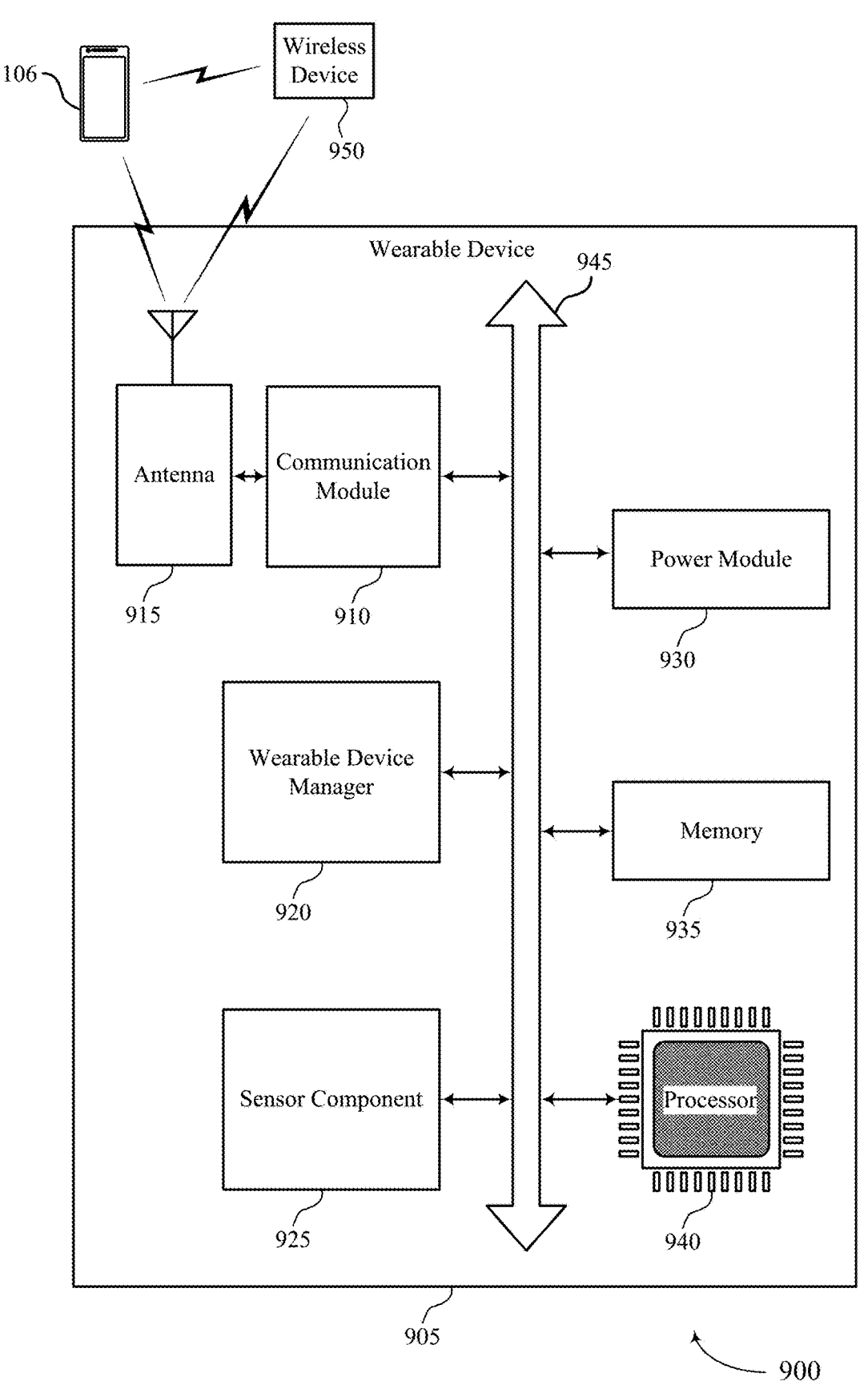
FIG. 9 shows a diagram of a system including a device that supports wearing detection techniques for wearable devices in accordance with aspects of the present disclosure.

FIG. 9 shows a diagram of a system 900 including a device 905 that supports wearing detection techniques for wearable devices in accordance with aspects of the present disclosure. The device 905 may be an example of or include the components of a device 705 as described herein. The device 905 may include an example of a wearable device such as a ring wearable device 104, as described herein. The device 905 may include components for bi-directional communications with a user device 106, a server 110, or both, such as a wearable device manager 920, a communication module 910, an antenna 915, a sensor component 925, a power module 930, a memory 935, a processor 940, and a wireless device 950. These components may be in electronic communication or otherwise coupled (e.g., operatively, communicatively, functionally, electronically, electrically) via one or more buses (e.g., a bus 945).

The wearable device manager 920 may support detecting contact with a wearable device in accordance with examples as disclosed herein. For example, the wearable device manager 920 may be configured as or otherwise support a means for directing light from a light source to a detector using an optical light guide of the wearable device, wherein the optical light guide comprises an optical interface configured to allow at least a portion of the directed light to escape the optical light guide based on a refractive property of a material contacting the optical interface. The wearable device manager 920 may be configured as or otherwise support a means for measuring, via the detector, an amount of escaped light which escaped the optical light guide, wherein the amount of escaped light is indicative of a level of surface contact at the optical interface of the optical light guide. The wearable device manager 920 may be configured as or otherwise support a means for controlling an activation of one or more sensors of the wearable device based at least in part on the amount of escaped light.

By including or configuring the wearable device manager 920 in accordance with examples as described herein, the device 905 may support techniques for a wearable device to utilize one or more light guides, light sources, and detectors to determine when skin contact is lost at one or more sensors of the wearable device, which may improve measurement accuracy as well as reduce power consumption at the wearable device.

The communication module 910 may manage input and output signals for the device 905 via the antenna 915. The communication module 910 may include an example of the communication module 220-b of the user device 106 shown and described in FIG. 2. In this regard, the communication module 910 may manage communications with the ring 104 and the server 110, as illustrated in FIG. 2. The communication module 910 may also manage peripherals not integrated into the device 905. In some cases, the communication module 910 may represent a physical connection or port to an external peripheral. In some cases, the communication module 910 may utilize an operating system such as iOS®, ANDROID®, MS-DOS®, MS-WINDOWS®, OS/2®, UNIX®, LINUX®, or another known operating system. In other cases, the communication module 910 may represent or interact with a wearable device (e.g., ring 104), modem, a keyboard, a mouse, a touchscreen, or a similar device. In some cases, the communication module 910 may be implemented as part of the processor 940. In some examples, a user may interact with the device 905 via the communication module 910, user interface component 925, or via hardware components controlled by the communication module 910.

In some cases, the device 905 may include a single antenna 915. However, in some other cases, the device 905 may have more than one antenna 915, which may be capable of concurrently transmitting or receiving multiple wireless transmissions. The communication module 910 may communicate bi-directionally, via the one or more antennas 915, wired, or wireless links as described herein. For example, the communication module 910 may represent a wireless transceiver and may communicate bi-directionally with another wireless transceiver. The communication module 910 may also include a modem to modulate the packets, to provide the modulated packets to one or more antennas 915 for transmission, and to demodulate packets received from the one or more antennas 915.

The user interface component 925 may manage data storage and processing in a database. In some cases, a user may interact with the user interface component 925. In other cases, the user interface component 925 may operate automatically without user interaction. The database may be an example of a single database, a distributed database, multiple distributed databases, a data store, a data lake, or an emergency backup database.

The memory 935 may include RAM and ROM. The memory 935 may store computer-readable, computer-executable software including instructions that, when executed, cause the processor 940 to perform various functions described herein. In some cases, the memory 935 may contain, among other things, a basic I/O (BIOS) which may control basic hardware or software operation such as the interaction with peripheral components or devices.

The processor 940 may include an intelligent hardware device, (e.g., a general-purpose processor, a digital signaling processor (DSP), a central processing unit (CPU), a microcontroller, an application-specific integrated circuit (ASIC), a field-programmable gate-array (FPGA), a programmable logic device, a discrete gate or transistor logic component, a discrete hardware component, or any combination thereof). In some cases, the processor 940 may be configured to operate a memory array using a memory controller. In other cases, a memory controller may be integrated into the processor 940. The processor 940 may be configured to execute computer-readable instructions stored in a memory 935 to perform various functions (e.g., functions or tasks supporting a method and system for sleep staging algorithms).

By including or configuring the wearable application 920 in accordance with examples as described herein, the device 905 may support techniques for a wearable device to utilize one or more light guides, light sources, and detectors to determine when skin contact is lost at one or more sensors of the wearable device, which may improve measurement accuracy as well as reduce power consumption at the wearable device.

The wearable application 920 may include an application (e.g., "app"), program, software, or other component which is configured to facilitate communications with a ring 104, server 110, other user devices 106, and the like. For example, the wearable application 920 may include an application executable on a user device 106 which is configured to receive data (e.g., physiological data) from a ring 104, perform processing operations on the received data, transmit and receive data with the servers 110, and cause presentation of data to a user 102.

FIG. 10 shows a flowchart illustrating a method 1000 that supports wearing detection techniques for wearable devices in accordance with aspects of the present disclosure. The operations of the method 1000 may be implemented by a wearable device or its components as described herein. For example, the operations of the method 1000 may be performed by a wearable device as described with reference to FIGS. 1 through 9. In some examples, a wearable device may execute a set of instructions to control the functional elements of the wearable device to perform the described functions. Additionally, or alternatively, the wearable device may perform aspects of the described functions using special-purpose hardware.

At 1005, the method may include directing light from a light source to a detector using an optical light guide of the wearable device, wherein the optical light guide comprises an optical interface configured to allow at least a portion of the directed light to escape the optical light guide based on a refractive property of a material contacting the optical interface. The operations of 1005 may be performed in accordance with examples as disclosed herein. In some examples, aspects of the operations of 1005 may be performed by a light source component 825 as described with reference to FIG. 8.

At 1010, the method may include measuring, via the detector, an amount of escaped light which escaped the optical light guide, wherein the amount of escaped light is indicative of a level of surface contact at the optical interface of the optical light guide. The operations of 1010 may be performed in accordance with examples as disclosed herein. In some examples, aspects of the operations of 1010 may be performed by a detector component 830 as described with reference to FIG. 8.

At 1015, the method may include controlling an activation of one or more sensors of the wearable device based at least in part on the amount of escaped light. The operations of 1015 may be performed in accordance with examples as disclosed herein. In some examples, aspects of the operations of 1015 may be performed by a sensor component 835 as described with reference to FIG. 8.

FIG. 11 shows a flowchart illustrating a method 1100 that supports wearing detection techniques for wearable devices in accordance with aspects of the present disclosure. The operations of the method 1100 may be implemented by a wearable device or its components as described herein. For example, the operations of the method 1100 may be performed by a wearable device as described with reference to FIGS. 1 through 9. In some examples, a wearable device may execute a set of instructions to control the functional elements of the wearable device to perform the described functions. Additionally, or alternatively, the wearable device may perform aspects of the described functions using special-purpose hardware.

At 1105, the method may include directing light from a light source to a detector using an optical light guide of the wearable device, wherein the optical light guide comprises an optical interface configured to allow at least a portion of the directed light to escape the optical light guide based on a refractive property of a material contacting the optical interface. The operations of 1105 may be performed in accordance with examples as disclosed herein. In some examples, aspects of the operations of 1105 may be performed by a light source component 825 as described with reference to FIG. 8.

At 1110, the method may include measuring, via the detector, an amount of escaped light which escaped the optical light guide, wherein the amount of escaped light is indicative of a level of surface contact at the optical interface of the optical light guide. The operations of 1110 may be performed in accordance with examples as disclosed herein. In some examples, aspects of the operations of 1110 may be performed by a detector component 830 as described with reference to FIG. 8.

At 1115, the method may include activating the one or more sensors of the wearable device based at least in part on the level of surface contact associated with the amount of escaped light satisfying a threshold level of surface contact. The operations of 1115 may be performed in accordance with examples as disclosed herein. In some examples, aspects of the operations of 1115 may be performed by a sensor component 835 as described with reference to FIG. 8.

At 1120, the method may include deactivating the one or more sensors of the wearable device based at least in part on the level of surface contact associated with the amount of escaped light failing to satisfy the threshold level of surface contact. The operations of 1120 may be performed in accordance with examples as disclosed herein. In some examples, aspects of the operations of 1120 may be performed by a sensor component 835 as described with reference to FIG. 8.

At 1125, the method may include controlling an activation of one or more sensors of the wearable device based at least in part on the amount of escaped light. The operations of 1125 may be performed in accordance with examples as disclosed herein. In some examples, aspects of the operations of 1125 may be performed by a sensor component 835 as described with reference to FIG. 8.

FIG. 12 shows a flowchart illustrating a method 1200 that supports wearing detection techniques for wearable devices in accordance with aspects of the present disclosure. The operations of the method 1200 may be implemented by a wearable device or its components as described herein. For example, the operations of the method 1200 may be performed by a wearable device as described with reference to FIGS. 1 through 9. In some examples, a wearable device may execute a set of instructions to control the functional elements of the wearable device to perform the described functions. Additionally, or alternatively, the wearable device may perform aspects of the described functions using special-purpose hardware.

At 1205, the method may include directing light from a light source to a detector using an optical light guide of the wearable device, wherein the optical light guide comprises an optical interface configured to allow at least a portion of the directed light to escape the optical light guide based on a refractive property of a material contacting the optical interface. The operations of 1205 may be performed in accordance with examples as disclosed herein. In some examples, aspects of the operations of 1205 may be performed by a light source component 825 as described with reference to FIG. 8.

At 1210, the method may include measuring, via the detector, an amount of escaped light which escaped the optical light guide, wherein the amount of escaped light is indicative of a level of surface contact at the optical interface of the optical light guide. The operations of 1210 may be performed in accordance with examples as disclosed herein. In some examples, aspects of the operations of 1210 may be performed by a detector component 830 as described with reference to FIG. 8.

At 1215, the method may include controlling an activation of one or more sensors of the wearable device based at least in part on the amount of escaped light. The operations of 1215 may be performed in accordance with examples as disclosed herein. In some examples, aspects of the operations of 1215 may be performed by a sensor component 835 as described with reference to FIG. 8.

At 1220, the method may include determining an orientation of the wearable device based at least in part on the amount of escaped light. The operations of 1220 may be performed in accordance with examples as disclosed herein. In some examples, aspects of the operations of 1220 may be performed by a wearable device orientation component 840 as described with reference to FIG. 8.

At 1225, the method may include causing a graphical user interface of a user device to display an indication of the orientation of the wearable device, an instruction to adjust the orientation of the wearable device, or both. The operations of 1225 may be performed in accordance with examples as disclosed herein. In some examples, aspects of the operations of 1225 may be performed by a user interface component 845 as described with reference to FIG. 8.

The method may include use of the contact sensing system as a UI for controlling the functions of the wearable device or associated software on external devices. For example, intentional rotation of the ring performed by the user could control a scrolling action on a mobile device application display or a series of taps on a specific side of the ring could activate a higher frequency PPG measurement of the ring for an exercise session.

It should be noted that the methods described above describe possible implementations, and that the operations and the steps may be rearranged or otherwise modified and that other implementations are possible. Furthermore, aspects from two or more of the methods may be combined.

A method for detecting contact with a wearable device is described. The method may include directing light from a light source to a detector using an optical light guide of the wearable device, wherein the optical light guide comprises an optical interface configured to allow at least a portion of the directed light to escape the optical light guide based on a refractive property of a material contacting the optical interface, measuring, via the detector, an amount of escaped light which escaped the optical light guide, wherein the amount of escaped light is indicative of a level of surface contact at the optical interface of the optical light guide, and controlling an activation of one or more sensors of the wearable device based at least in part on the amount of escaped light.

An apparatus for detecting contact with a wearable device is described. The apparatus may include a processor, memory coupled with the processor, and instructions stored in the memory. The instructions may be executable by the processor to cause the apparatus to direct light from a light source to a detector using an optical light guide of the wearable device, wherein the optical light guide comprises an optical interface configured to allow at least a portion of the directed light to escape the optical light guide based on a refractive property of a material contacting the optical interface, measure, via the detector, an amount of escaped light which escaped the optical light guide, wherein the amount of escaped light is indicative of a level of surface contact at the optical interface of the optical light guide, and control an activation of one or more sensors of the wearable device based at least in part on the amount of escaped light.

Another apparatus for detecting contact with a wearable device is described. The apparatus may include means for directing light from a light source to a detector using an optical light guide of the wearable device, wherein the optical light guide comprises an optical interface configured to allow at least a portion of the directed light to escape the optical light guide based on a refractive property of a material contacting the optical interface, means for measuring, via the detector, an amount of escaped light which escaped the optical light guide, wherein the amount of escaped light is indicative of a level of surface contact at the optical interface of the optical light guide, and means for controlling an activation of one or more sensors of the wearable device based at least in part on the amount of escaped light.

A non-transitory computer-readable medium storing code for detecting contact with a wearable device is described. The code may include instructions executable by a processor to direct light from a light source to a detector using an optical light guide of the wearable device, wherein the optical light guide comprises an optical interface configured to allow at least a portion of the directed light to escape the optical light guide based on a refractive property of a material contacting the optical interface, measure, via the detector, an amount of escaped light which escaped the optical light guide, wherein the amount of escaped light is indicative of a level of surface contact at the optical interface of the optical light guide, and control an activation of one or more sensors of the wearable device based at least in part on the amount of escaped light.

In some examples of the method, apparatuses, and non-transitory computer-readable medium described herein, controlling the activation of one or more sensors may include operations, features, means, or instructions for activating the one or more sensors of the wearable device based at least in part on the level of surface contact associated with the amount of escaped light satisfying a threshold level of surface contact and deactivating the one or more sensors of the wearable device based at least in part on the level of surface contact associated with the amount of escaped light failing to satisfy the threshold level of surface contact.

Some examples of the method, apparatuses, and non-transitory computer-readable medium described herein may further include operations, features, means, or instructions for directing additional light from an additional light source to an additional detector using an additional optical light guide of the wearable device, wherein the additional optical light guide comprises an additional optical interface, measuring, via the additional detector, an additional amount of escaped light which escaped the additional optical light guide, wherein the additional amount of escaped light may be indicative of an additional level of surface contact at the additional optical interface of the additional optical light guide, and controlling the activation of one or more sensors of the wearable device based at least in part on the amount of escaped light, the additional amount of escaped light, or both.

In some examples of the method, apparatuses, and non-transitory computer-readable medium described herein, controlling the activation of the one or more sensors may include operations, features, means, or instructions for controlling a first activation of a first subset of the one or more sensors of the wearable device based at least in part on the amount of escaped light and controlling a second activation of a second subset of the one or more sensors of the wearable device based at least in part on the additional amount of escaped light.

Some examples of the method, apparatuses, and non-transitory computer-readable medium described herein may further include operations, features, means, or instructions for determining an orientation of the wearable device based at least in part on the amount of escaped light and causing a GUI of a user device to display an indication of the orientation of the wearable device, an instruction to adjust the orientation of the wearable device, or both.

In some examples of the method, apparatuses, and non-transitory computer-readable medium described herein, the optical interface may be configured to allow at least a portion of the directed light to escape the optical light guide based on a difference between the refractive property of the material and an additional refractive property of the optical light guide.

In some examples of the method, apparatuses, and non-transitory computer-readable medium described herein, the directed light comprises a plurality of wavelengths and the method, apparatuses, and non-transitory computer-readable medium may include further operations, features, means, or instructions for measuring, via the detector, a plurality of amounts of escaped light which escaped the optical light guide corresponding to the plurality of wavelengths and performing one or more spectral analysis operations based at least in part on the plurality of amounts of escaped light.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. F or example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for detecting contact with a wearable ring device configured to be worn on a finger of a user, comprising:

directing first light from one or more light sources to one or more detectors using a first optical light guide that spans at least a first radial portion of an inner curved surface of the wearable ring device, wherein the first optical light guide comprises a first optical interface configured to allow at least a portion of the first light to escape the first optical light guide based on a refractive property of a material contacting the first optical interface;

directing second light from the one or more light sources to the one or more detectors using a second optical light guide that spans at least a second radial portion of the inner curved surface of the wearable ring device;

measuring, via the one or more detectors, a first amount of escaped light which escaped the first optical light guide and a second amount of escaped light which escaped the second optical light guide, wherein the first amount of escaped light is indicative of a first level of surface contact with the first radial portion of the inner curved surface, and wherein the second amount of escaped light is indicative of a second level of surface contact with the second radial portion of the inner curved surface;

selecting one or more sensors of the wearable ring device associated with at least one of the first radial portion and the second radial portion based at least in part on the first amount of escaped light and the second amount of escaped light, wherein selecting the one or more sensors comprises:

controlling a first activation of a first subset of the one or more sensors of the wearable ring device associated with the first radial portion based at least in part on the first amount of escaped light; and controlling a second activation of a second subset of the one or more sensors of the wearable ring device associated with the second radial portion based at least in part on the second amount of escaped light; and acquiring physiological data from the user via the one or more sensors based at least in part on the selecting.

2. The method of claim 1, wherein selecting the one or more sensors comprises:

activating one or more first sensors of the wearable ring device associated with the first radial portion based at least in part on the first level of surface contact associated with the first amount of escaped light satisfying a threshold level of surface contact; and deactivating one or more second sensors of the wearable ring device associated with the second radial portion based at least in part on the second level of surface contact associated with the second amount of escaped light failing to satisfy the threshold level of surface contact.

3. The method of claim 1, further comprising:

determining an orientation of the wearable ring device based at least in part on the first amount of escaped light, the second amount of escaped light, or both; and causing a graphical user interface of a user device to display an indication of the orientation of the wearable ring device, an instruction to adjust the orientation of the wearable ring device, or both.

4. The method of claim 1, wherein the first optical interface is configured to allow at least a portion of the first light to escape the first optical light guide based on a difference between the refractive property of the material and a second refractive property of the first optical light guide.

5. The method of claim 1, wherein the first light comprises a plurality of wavelengths, the method further comprising:

measuring, via the one or more detectors, a plurality of amounts of escaped light which escaped the first optical light guide corresponding to the plurality of wavelengths; and performing one or more spectral analysis operations based at least in part on the plurality of amounts of escaped light.

6. An apparatus for a wearable ring device configured to be worn on a finger of a user, comprising:

a plurality of sensors configured to acquire physiological data from the user associated with the wearable ring device, wherein the plurality of sensors comprises a light-emitting diode and a photodetector, and;

a light guide apparatus for detecting contact with the wearable ring device, the light guide apparatus comprising:

one or more light sources, wherein the light-emitting diode comprises the one or more light sources;

one or more detectors;

a first optical light guide that spans at least a first radial portion of an inner curved surface of the wearable ring device and that is configured to direct first light from the one or more light sources to the one or more detectors, wherein the first optical light guide comprises a first optical interface configured to allow at least a portion of the first light to escape the first optical light guide based on a refractive property of a material contacting the first optical interface; and a second optical light guide that spans at least a second radial portion of the inner curved surface of the wearable ring device and that is configured to direct second light from the one or more light sources to the one or more detectors; and one or more controllers configured to:

measure, via the one or more detectors, a first amount of escaped light which escaped the first optical light guide and a second amount of escaped light which escaped the second optical light guide, wherein the first amount of escaped light is indicative of a first level of surface contact with the first radial portion of the inner curved surface, and wherein the second amount of escaped light is indicative of a second level of surface contact with the second radial portion of the inner curved surface;

select one or more sensors of the wearable ring device associated with at least one of the first radial portion and the second radial portion based at least in part on the first amount of escaped light and the second amount of escaped light; and acquire physiological data from the user via the one or more sensors based at least in part on the selection.

7. The apparatus of claim 6, wherein the plurality of sensors comprises:

a plurality of light-emitting diodes positioned at a first plurality of radial positions along the inner curved surface of the wearable ring device; and a plurality of photodetectors positioned at a second plurality of radial positions along the inner curved surface of the wearable ring device, the plurality of photodetectors configured to receive light emitted from the plurality of light-emitting diodes.

8. The apparatus of claim 6, wherein the one or more light sources are located at a first radial position on the wearable ring device relative to an axis of the wearable ring device, wherein a first detector of the one or more detectors is located at a second radial position on the wearable ring device relative to the axis of the wearable ring device, and wherein the first optical light guide is configured to optically couple the one or more light sources to the first detector along the inner curved surface.

9. The apparatus of claim 6, wherein the plurality of sensors comprises one or more photodetectors, one or more green light-emitting diodes, one or more red light-emitting diodes, one or more infrared light sources, or any combination thereof, and wherein the one or more light sources of the light guide apparatus comprises a blue light-emitting diode, a micro-light-emitting diode, a laser diode, or any combination thereof.

10. An apparatus for detecting contact with a wearable ring device configured to be worn on a finger of a user, comprising:

one or more processors;

memory coupled with the one or more processors; and instructions stored in the memory and executable by the one or more processors to cause the apparatus to:

direct first light from one or more light sources to one or more detectors using a first optical light guide that spans at least a first radial portion of an inner curved surface of the wearable ring device, wherein the first optical light guide comprises a first optical interface configured to allow at least a portion of the first light to escape the first optical light guide based on a refractive property of a material contacting the first optical interface;

direct second light from the one or more light sources to the one or more detectors using a second optical light guide that spans at least a second radial portion of the inner curved surface of the wearable ring device;

measure, via the one or more detectors, a first amount of escaped light which escaped the first optical light guide and a second amount of escaped light which escaped the second optical light guide, wherein the first amount of escaped light is indicative of a first level of surface contact with the first radial portion of the inner curved surface, and wherein the second amount of escaped light is indicative of a second level of surface contact with the second radial portion of the inner curved surface;

select one or more sensors of the wearable ring device associated with at least one of the first radial portion and the second radial portion based at least in part on the first amount of escaped light and the second amount of escaped light, wherein, to select the one or more sensors, the one or more processors are configured to:

control a first activation of a first subset of the one or more sensors of the wearable ring device associated with the first radial portion based at least in part on the first amount of escaped light; and control a second activation of a second subset of the one or more sensors of the wearable ring device associated with the second radial portion based at least in part on the second amount of escaped light; and acquire physiological data from the user via the one or more sensors based at least in part on the selection.

11. The apparatus of claim 10, wherein the instructions to select the one or more sensors are executable by the one or more processors to cause the apparatus to:

activate one or more first sensors of the wearable ring device associated with the first radial portion based at least in part on the first level of surface contact associated with the first amount of escaped light satisfying a threshold level of surface contact; and deactivate one or more second sensors of the wearable ring device associated with the second radial portion based at least in part on the second level of surface contact associated with the second amount of escaped light failing to satisfy the threshold level of surface contact.

12. The apparatus of claim 10, wherein the instructions are further executable by the one or more processors to cause the apparatus to:

determine an orientation of the wearable ring device based at least in part on the first amount of escaped light, the second amount of escaped light, or both; and cause a graphical user interface of a user device to display an indication of the orientation of the wearable ring device, an instruction to adjust the orientation of the wearable ring device, or both.

13. The apparatus of claim 10, wherein the first optical interface is configured to allow at least a portion of the first light to escape the first optical light guide based on a difference between the refractive property of the material and a second refractive property of the first optical light guide.

14. The apparatus of claim 10, wherein the first light comprises a plurality of wavelengths, and the instructions are further executable by the one or more processors to cause the apparatus to:

measure, via the one or more detectors, a plurality of amounts of escaped light which escaped the first optical light guide corresponding to the plurality of wavelengths; and perform one or more spectral analysis operations based at least in part on the plurality of amounts of escaped light.

* * * * *